US007884102B2

(12) United States Patent
Dolle et al.

(10) Patent No.: US 7,884,102 B2
(45) Date of Patent: *Feb. 8, 2011

(54) SUBSTITUTED PIPERIDINE COMPOUNDS AND METHODS OF THEIR USE

(75) Inventors: Roland Ellwood Dolle, King of Prussia, PA (US); Bertrand Le Bourdonnec, East Fallowfield Township, PA (US)

(73) Assignee: Adolor Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/110,915

(22) Filed: Apr. 28, 2008

(65) Prior Publication Data

US 2008/0306071 A1    Dec. 11, 2008

Related U.S. Application Data

(63) Continuation of application No. 10/390,522, filed on Mar. 17, 2003, now Pat. No. 7,381,721.

(51) Int. Cl.
| | |
|---|---|
| *A61K 31/535* | (2006.01) |
| *A61K 31/425* | (2006.01) |
| *C07D 405/00* | (2006.01) |
| *C07D 211/32* | (2006.01) |

(52) U.S. Cl. ............... 514/236.5; 514/256; 514/318; 514/321; 514/322; 514/323; 514/324; 514/326; 546/210; 546/211; 546/213; 546/214; 546/224; 546/226; 546/230; 546/231; 546/232; 546/233; 546/234; 546/239; 546/246; 546/259

(58) Field of Classification Search ............... None
See application file for complete search history.

(56) References Cited

U.S. PATENT DOCUMENTS

| | | | |
|---|---|---|---|
| 4,176,186 | A | 11/1979 | Goldberg et al. |
| 4,191,771 | A | 3/1980 | Zimmerman |
| 4,931,558 | A | 6/1990 | Barnett |
| 4,987,126 | A | 1/1991 | Bargiotti et al. |
| 5,159,081 | A | 10/1992 | Cantrell et al. |
| 5,250,542 | A | 10/1993 | Cantrell et al. |
| 5,270,328 | A | 12/1993 | Cantrell et al. |
| 5,434,171 | A | 7/1995 | Frank et al. |
| 5,972,954 | A | 10/1999 | Foss et al. |
| 6,812,236 | B2 | 11/2004 | Gibson et al. |

FOREIGN PATENT DOCUMENTS

| | | |
|---|---|---|
| EP | 1072592 A2 | 1/2001 |
| WO | 02/053533 A2 | 7/2002 |

OTHER PUBLICATIONS

Bagnol, D., et al., "Cellular localization and distribution of the cloned MU and KAPPA Opioid receptors in rat gastrointestinal tract," *Neuroscience*, 1997, 81(2), 579-591.

Gabnol, D., et al., "Changes in enkephalin immunoreactivity of sympathetic ganglia and digestive tract of the cat after splanchnic nerve ligation," *Regul. Pept.*, 1993, 47, 259-273.

Bhargava, H.N., et al., "Effect of nitric oxide synthase inhibition on tolerance to the analgesic action of D-Pen$^2$, D-Pen$^5$ enkephalin and morphine in the mouse," *Neuropeptides*, 1996, 30(3), 219-223.

Bilsky, E.J., et al., "Effects of naloxone and D-Phe-Cys-Tyr-D-Trp-Arg-Thr-Pen-Thr-NH2 and the protein kinase inhibitors H7 and H8 on acute morphine dependence and antinociceptive tolerance in mice," *J. PHarmacol Exp. Ther.*, 1996, 277(1), 484-490.

Dorland's Illustrated Medical Dictionary, 27$^{th}$ Ed., *W.B. Saunders Company*, Phila, PA., 1988, p. 816.

Dorland's Illustrated Medical Dictionary, 27$^{th}$ Ed., *W.B. Saunders Company*, Phila, PA., 1988, p. 375.

Dourish, C.T., et al, "Enhancement of morphine analgesia and prevention of morphine tolderance in the rat by the cholecystokinin antagonist L-364, 718," *Eur. J. Pharmacol*, 1988, 147, 469-472.

Koch, T. R., et al., "Inhibitory neuropeptides and intrinsic inhibitory innervation of descending human colon," *Digestive Diseases and Sciences*, Jun. 1991, 36(6), 712-718.

Kreek, M., et al., "Naloxone, a specific Opioid antagonist, reverses chronic idiopathic constipation" *J. Lancet*, Feb. 5, 1983, 261-262.

Livingston, E.H., et al, "Postoperative ileus," *Digestive Diseases and Sciences*, Jan. 1990, 35(1), 121-132.

Mack, D.J., et al "Paralytic ileus: response to naloxone," *Br. J. Surg.*, Oct. 1989, 76(10), p. 1101.

Mao, M.J., et al., "Oral administration of dextromethorphan prevents the development of morphine tolerance and dependence in rates," *Int'l Assoc. for the Study of Pain*, 1996, 67, 361-368.

Mitch, C.H., et al., "Synthesis and absolute configuration of LY255582, a potent Opioid antagonist," *J. Org. Chem.*, 1991, 56.

Nichols, M.L., et al., Enhancement of the antiallodynic and antinociceptive efficacy of spinal morphine by antisera to dynorphin A (1-13) or MK-801 in a nerve-ligation model of peripheral neuropathy, *Pain*, 1997, 69, 317-322.

Orchin, M., et al., *The Vocabulary of Organic Chemistry*, 1980, John Wiley & Sons, Inc., p. 126-127.

Physicians' Desk Reference, 1999.

Reisine, T., et al., "Opioid analgensics and antagonists," *Goodman & Gillman's The Pharmacological Basis of Therapeutics*, 9$^{th}$ Ed., 1996, Chapter 23, 521-555.

Remington's Pharmaceutical Sciences, *Mack Pub. Col*, Easton, PA, 1980.

Resnick, J., et al., "Delayed gastric emptying and postoperative ileus after nongastreic abdominal surgery: Part 1," *Am. J. of Gastroeterology*, 1997, 92(5), 751-762.

Resnick, J., et al., "Delayed gastric emptying and postoperative ileus after nongastreic abdominal surgery: Part 1," *Am. J. of Gastroeterology*, 1997, 92(6), 934-940.

(Continued)

*Primary Examiner*—Janet L. Andres
*Assistant Examiner*—Raymond Covington
(74) *Attorney, Agent, or Firm*—Feldman Gale, P.A.; David A. Cherry

(57) ABSTRACT

3,4-Disubstituted-4-aryl-piperidine compounds are disclosed. Pharmaceutical compositions containing the 3,4-disubstituted-4-aryl-piperidine compounds and methods of their pharmaceutical uses are also disclosed. The compounds disclosed are useful, inter alia, as antagonists of opioid receptors.

55 Claims, No Drawings

OTHER PUBLICATIONS

Schang, J.C., et al., "Beneficial effects of naloxone in a patent with intestinal pseudoobstruction," *Am. J. Gastroenerol.*, 1985, 80(6), 407-411.

Schuller, A.G.P., et al., "M6G, but not morphine, inhibits GI transit in mu opioid receptor deficient mice," *Society of Neuroscience Abstracts*, 1998, 24, p. 524.

Werner, J.A., et al., "Synthesis of *trans*-3,4-dimethyl-4-(3-hydroxyphenyl) piperidine Opioid antagonists: application of the *Cis*-thermal elimination of carbonates to alkalid synthesis," *J. Org. Chem.*, 1996, 61, 587-597.

Wittert, G., et al., "Tissue distribution of Opioid receptor gene expression in the rat," *Biochemical & Biophysical Res. Comm.*, 1996, 218, 877-881.

US 7,884,102 B2

SUBSTITUTED PIPERIDINE COMPOUNDS AND METHODS OF THEIR USE

CROSS REFERENCE TO RELATED APPLICATION

This application is a continuation of U.S. application Ser. No. 10/390,522, filed Mar. 17, 2003, now allowed, the disclosure of which is hereby incorporated herein by reference, in its entirety.

FIELD OF THE INVENTION

The present invention relates to compounds that affect the opioid receptor system and, more particularly, to 3,4-disubstituted-4-aryl-piperidine compounds and pharmaceutical compositions containing such compounds that are, inter alia, antagonists of opioid receptors.

BACKGROUND OF THE INVENTION

It is well known that opioid drugs target three types of endogenous opioid receptors (i.e., $\mu$, $\delta$, and $\kappa$ receptors) in biological systems. Many opiates, such as morphine, are $\mu$ opioid agonists that are often used as analgesics for the treatment of severe pain due to their activation of $\mu$ opioid receptors in the brain and central nervous system (CNS). Opioid receptors are, however, not limited to the CNS, and may be found in other tissues throughout the body, i.e., peripheral to the CNS. A number of side effects of opioid drugs may be caused by activation of these peripheral receptors. For example, administration of $\mu$ opioid agonists often results in intestinal dysfunction due to the large number of receptors in the wall of the gut (Wittert, G., Hope, P. and Pyle, D., *Biochemical and Biophysical Research Communications* 1996, 218, 877-881; Bagnol, D., Mansour, A., Akil, A. and Watson, S. *J., Neuroscience* 1997, 81, 579-591). Specifically, opioids are generally known to cause nausea and vomiting, as well as inhibition of normal propulsive gastrointestinal function in animals and man (Reisine, T., and Pasternak, G., Goodman & Gilman's *The Pharmacological Basis of Therapeutics, Ninth Edition* 1996, 521-555), resulting in side effects such as, for example, constipation.

Recent evidence has indicated that naturally-occurring endogenous opioid compounds may also affect propulsive activity in the gastrointestinal (GI) tract. Met-enkephalin, which activates $\mu$ and $\delta$ receptors in both the brain and gut, is one of several neuropeptides found in the GI tract (Koch, T. R., Carney, J. A., Go, V. L., and Szurszewski, J. H., *Digestive Diseases and Sciences* 1991, 36, 712-728). Additionally, receptor knockout techniques have shown that mice lacking $\mu$ opioid receptors may have faster GI transit times than wild-type mice, suggesting that endogenous opioid peptides may tonically inhibit GI transit in normal mice (Schuller, A. G. P., King, M., Sherwood, A. C., Pintar, J. E., and Pasternak, G. W., *Society of Neuroscience Abstracts* 1998, 24, 524). Studies have shown that opioid peptides and receptors located throughout the GI tract may be involved in normal regulation of intestinal motility and mucosal transport of fluids in both animals and man (Reisine, T., and Pasternak, G., Goodman & Gilman's *The Pharmacological Basis of Therapeutics, Ninth Edition* 1996, 521-555). Other studies show that the sympathetic nervous system may be associated with endogenous opioids and control of intestinal motility (Bagnol, D., Herbrecht, F., Jule, Y., Jarry, T., and Cupo, A., *Regul. Pept.* 1993, 47, 259-273). The presence of endogenous opioid compounds associated with the GI tract suggests that an abnormal physiological level of these compounds may lead to bowel dysfunction.

It is a common problem for patients having undergone surgical procedures, especially surgery of the abdomen, to suffer from a particular bowel dysfunction called post-surgical (or post-operative) ileus. "Ileus," as used herein, refers to the obstruction of the bowel or gut, especially the colon. See, e.g., *Dorland's Illustrated Medical Dictionary*, 27th ed., p. 816, (W.B. Saunders Company, Philadelphia, Pa., 1988). Ileus should be distinguished from constipation, which refers to infrequency of or difficulty in feces evacuation. See, e.g., *Dorland's Illustrated Medical Dictionary*, 27th ed., p. 375, (W.B. Saunders Company, Philadelphia 1988). Ileus may be diagnosed by the disruption of normal coordinated movements of the gut, resulting in failure of intestinal contents propulsion. See, e.g., Resnick, J. Am. *J. of Gastroenterology* 1997, 92, 751 and Resnick, J. Am. *J. of Gastroenterology*, 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, Jr., E. D., *Digestive Diseases and Sciences* 1990, 35, 121). Similarly, post-partum ileus is a common problem for women in the period following childbirth, and is thought to be caused by similar fluctuations in natural opioid levels as a result of birthing stress.

Gastrointestinal dysmotility associated with post-surgical ileus is generally most severe in the colon and typically lasts for 3 to 5 days. The administration of opioid analgesics to a patient after surgery may often contribute to bowel dysfunction, thereby delaying recovery of normal bowel function. Since virtually all patients receive opioid analgesics, such as morphine or other narcotics, for pain relief after surgery, particularly major surgery, current post-surgical pain treatment may actually slow recovery of normal bowel function, resulting in a delay in hospital discharge and increasing the cost of medical care.

Post-surgical and post-partum ileus may also occur in the absence of exogenous opioid agonists. It would be of benefit to inhibit the natural activity of endogenous opioids during and/or after periods of biological stress, such as surgery and childbirth, so that ileus and related forms of bowel dysfunction can be prevented and/or treated. Currently, therapies for ileus include functional stimulation of the intestinal tract, stool softeners, laxatives, lubricants, intravenous hydration, and nasogastric decompression. These prior art methods suffer from drawbacks, for example, as lacking specificity for post-surgical or post-partum ileus. And these prior art methods offer no means for prevention. If ileus could be prevented, hospital stays, recovery times, and medical costs would be significantly decreased, in addition to the benefit of minimizing patient discomfort. Thus, drugs that selectively act on opioid receptors in the gut would be ideal candidates for preventing and/or treating post-surgical and post-partum ileus. Of those, drugs that do not interfere with the effects of opioid analgesics in the CNS would be of special benefit in that they may be administered simultaneously for pain management with limited side effects.

Peripheral opioid antagonists that do not cross the blood-brain barrier into the CNS are known in the literature and have been tested in relation to their activity on the GI tract. In U.S. Pat. Nos. 5,250,542, 5,434,171, 5,159,081, and 5,270,328, peripherally selective piperidine-N-alkylcarboxylate opioid antagonists are described as being useful in the treatment of idiopathic constipation, irritable bowel syndrome and opioid-induced constipation. Also, U.S. Pat. No. 4,176,186 describes quaternary derivatives of noroxymorphone (i.e., methylnaltrexone) that are said to prevent or relieve the intestinal immobility side-effect of narcotic analgesics without reducing analgesic effectiveness. U.S. Pat. No. 5,972,954 describes the use of methylnaltrexone, enteric coated methylnaltrexone, or other quaternary derivatives of noroxymorphone for preventing and/or treating opioid- and/or nonopioid-induced side effects associated with opioid administration.

General opioid antagonists, such as naloxone and naltrexone, have also been implicated as being useful in the treatment of GI tract dysmotility. For example, U.S. Pat. No. 4,987,126 and Kreek, M. J. Schaefer, R. A., Hahn, E. F., Fishman, J. *Lancet* 1983, 1(8319), 261 disclose naloxone and other morphinan-based opioid antagonists (i.e., naloxone, naltrexone) for the treatment of idiopathic gastrointestinal dysmotility. In addition, naloxone has been shown to effectively treat non-opioid induced bowel obstruction, implying that the drug may act directly on the GI tract or in the brain (Schang, J. C., Devroede, G. *Am. J. Gastroenerol.* 1985, 80(6), 407). Furthermore, it has been implicated that naloxone may provide therapy for paralytic ileus (Mack, D. J. Fulton, J. D. *Br. J. Surg.* 1989, 76(10), 1101). However, it is well known that activity of naloxone and related drugs is not limited to peripheral systems and may interfere with the analgesic effects of opioid narcotics.

Inasmuch as post-surgical and post-partum ileus, for example, are common illnesses that add to the cost of health care and as yet have no specific treatments, there is a need for a specific and effective remedy. The majority of currently known opioid antagonist therapies is not peripherally selective and has the potential for undesirable side effects resulting from penetration into the CNS. Given the estimated 21 million inpatient surgeries and 26 million outpatient surgeries each year, and an estimate of 4.7 million patients experiencing post-surgical ileus, methods involving opioid antagonists that are not only specific for peripheral systems, but specific for the gut, are desirable for treating post-surgical and post-partum ileus.

There is still an unfulfilled need for compounds that may be used in methods to antagonize opioid receptors, particularly where undesirable symptoms or conditions are side effects of administering exogenous opioids. The present invention is directed to these, as well as other important ends.

SUMMARY OF THE INVENTION

Accordingly, the present invention is directed, in part, to novel pharmaceutically active compounds of formula I:

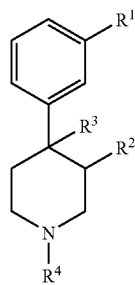

I wherein:
$R^1$ is —C(=O)OR$^5$, —C(=O)NR$^6$R$^7$, —NR$^6$R$^7$, or —CH$_2$OR$^5$;
$R^2$ and $R^3$ are each independently alkyl or alkenyl;
$R^4$ is:
H,
cycloalkyl,
heterocycloalkyl, or
$C_{1-10}$ alkyl which is substituted with at least one:
  substituted aryl, wherein at least one of said aryl substituents is other than OH, nitro, amino, halo, CN, CH$_2$CN, CONH$_2$, $C_{1-4}$ alkyl, $C_{1-4}$ alkoxy, or $C_{1-5}$ alkanoyl (which latter three groups are optionally substituted by one or more halo atoms),
  aryloxyaryl,
  -aryl-N(H)R$^b$
  -aryl-N(R$^b$)R$^b$,
  heteroarylaryl,
  alkoxyaryl, wherein the carbon chain of said alkoxy is interrupted by a nitrogen atom,
  substituted alkoxyaryl, provided that when one or more substituents are present on the alkoxy group, at least one of said substituents is other than halo,
  substituted cycloalkyl,
  RS(=O)$_p$ substituted heteroaryl,
  RS(=O)$_p$ substituted heterocycloalkyl,
  RS(=O)$_p$ substituted aryl,
  heterocycloalkylheteroaryl,
  heteroarylheteroaryl,
  bicycloalkyl,
  bicycloalkenyl,
  carboxy,
  —CO$_2$R$^a$,
  —C(=O)N(R$^{6a}$)—R$^{6b}$—CO$_2$H,
  —C(=O)N(R$^{6a}$)—R$^{6b}$—CO$_2$R,
  —C(=O)N(R$^{6a}$)—R$^{6b}$—C(=O)NR$^{7a}$R$^{7b}$,
  —N(R$^{7c}$)C(=O)R$^{7d}$,
  —N(R$^{7c}$)S(=O)$_2$R$^{7d}$,
  aralkoxyaryl,
  substituted arylheteroaryl, or
  substituted alkoxyheteroaryl, provided that when one or more substituents are present on the alkoxy group, at least one of said substituents is other than halo;
p is 0, 1, or 2;
R is alkyl, aralkyl, or aryl;
$R^a$ is H, alkyl, alkenyl, cycloalkyl, aryl, or heteroaryl, provided that $R^a$ is not $C_{1-6}$ alkyl;
each $R^b$ is independently alkyl, cycloalkyl, aralkyl, or aryl,
$R^{6a}$ is H, alkyl, aralkyl, cycloalkyl, alkenyl, aryl, heteroaralkyl, or heteroaryl;
$R^{6b}$ is lower alkylene, or lower aralkylene or, together with the nitrogen atom to which they are attached, $R^{6a}$ and $R^{6b}$ form a 4- to 7-membered heterocycloalkyl ring;
$R^{7a}$ and $R^{7b}$ are each independently H, alkyl, cycloalkyl, heterocycloalkyl, heteroaryl, aralkyl, or aryl, or together with the nitrogen atom to which they are attached, $R^{7a}$ and $R^{7b}$ form a 4- to 7-membered heterocycloalkyl ring, provided that at least one of $R^{7a}$ and $R^{7b}$ is other than H;
$R^{7c}$ and $R^{7d}$ are each independently H, alkyl, cycloalkyl, heterocycloalkyl, heteroaryl, aralkyl, or aryl;
$R^5$ is H or alkyl; and
each is $R^6$ and $R^7$ independently H, alkyl, or —C(=O) R, or together with the nitrogen atom to which they are attached, $R^6$ and $R^7$ form a 4- to 7-membered heterocycloalkyl ring, provided that no more than one of $R^6$ and $R^7$ is —C(=O)R, and provided that when $R^1$ is $NR^6R^7$, $R^4$ can also be aralkyl;

or a stereoisomer, prodrug, pharmaceutically acceptable salt, hydrate, solvate, acid salt hydrate, N-oxide or isomorphic crystalline form thereof, provided that $R^2$ and $R^3$ are not in the cis stereoisomer conformation when both $R^2$ and $R^3$ are methyl.

In another embodiment, the invention is directed to pharmaceutical compositions comprising a pharmaceutically acceptable carrier and an effective amount of a compound of formula I.

In yet another embodiment, the invention is directed to methods for binding opioid receptors, preferably μ or κ opioid receptors, in a patient in need thereof.

In other embodiments, the invention is directed to methods for binding opioid receptors, where the 3,4-disubstituted-4-aryl-piperidine compound exhibits activity toward the opioid receptors (selected from μ, κ, or combinations thereof).

In some preferred embodiments, the invention is directed to methods where the patient is in need of prevention or treatment of a condition, disease or undesirable side effect caused by an endogenous or exogenous opioid.

In a particularly preferred embodiment, the invention is directed to methods for preventing or treating gastrointestinal dysfunction.

In yet another preferred embodiment, the invention is directed to methods of preventing or treating pain, comprising the step of:

administering to a patient in need thereof, a composition, comprising an effective amount of an opioid; and an effective amount of a compound of formula I.

DETAILED DESCRIPTION OF ILLUSTRATIVE EMBODIMENTS

As employed above and throughout the disclosure, the following terms, unless otherwise indicated, shall be understood to have the following meanings.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkylene" refers to a bivalent alkyl radical having the general formula —$(CH_2)_n$—, where n is 1 to 10. Non-limiting examples include methylene, trimethylene, pentamethylene, and hexamethylene. Alkylene groups can be optionally substituted. The term "lower alkylene" herein refers to those alkylene groups having from about 1 to about 6 carbon atoms.

As used herein, "aralkylene" refers to a bivalent alkyl radical having the general formula —$(CH_2)_n$—, wherein any one of the hydrogens on the alkylene radical is replaced by an aryl group, and where n is 1 to 10. Aralkylene groups can be optionally substituted. Non-limiting examples include phenylmethylene, 2-phenyltrimethylene, 3-(p-anisyl)-pentamethylene, and 2-(m-trifluoromethylphenyl)-hexamethylene. Aralkylene groups can be substituted or unsubstituted. The term "lower aralkylene" herein refers to those aralkylene groups having from about 1 to about 6 carbon atoms in the alkylene portion of the aralkylene group.

As used herein, "alkenyl" refers to an alkyl group having one or more double bonds, wherein alkyl is as previously defined. Alkenyl groups can be optionally substituted.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred. Aralkyl groups can be optionally substituted. Non-limiting examples include, for example, benzyl, diphenylmethyl, triphenylmethyl, phenylethyl, and diphenylethyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. groups include, but are not limited to, cyclopropyl, cyclobutyl, cyclopentyl, cyclohexyl, cyclooctyl, and adamantyl.

As used herein, "alkylcycloalkyl" refers to an optionally substituted ring system comprising a cycloalkyl group having one or more alkyl substituents. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Examples of heterocycloalkyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4,-tetrahydroquinolyl, octahydro-[2]pyrindinyl, decahydro-cycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro[4.7]dodecane.

As used herein, the term "alkoxy" refers to an optionally substituted alkyl-O— group wherein alkyl is as previously defined. Exemplary alkoxy groups include methoxy, ethoxy, n-propoxy, i-propoxy, n-butoxy, and heptoxy.

As used herein, the term "aryloxy" refers to an optionally substituted aryl-O— group wherein aryl is as previously defined. Exemplary aryloxy groups include phenoxy and naphthoxy.

As used herein, the term "aralkoxy" refers to an optionally substituted aralkyl-O-group wherein aralkyl is as previously defined. Exemplary aralkoxy groups include benzyloxy, 1-phenylethoxy, 2-phenylethoxy, and 3-naphthylheptoxy.

As used herein, the term "aryloxyaryl" refers to an aryl group with an aryloxy substituent wherein aryloxy and aryl are as previously defined. Aryloxyaryl groups can be optionally substituted. Exemplary aryloxyaryl groups include phenoxyphenyl, and naphthoxyphenyl.

As used herein, the term "heteroarylaryl" refers to an aryl group with a heteroaryl substituent wherein heteroaryl and aryl are as previously defined. Heteroarylaryl groups can be optionally substituted. Exemplary heteroarylaryl groups include 3-pyridylphenyl, 2-quinolylnaphthalenyl, and 2-pyrrolylphenyl.

As used herein, the term "alkoxyaryl" refers to an aryl group bearing an alkoxy substituent wherein alkoxy and aryl are as previously defined. Alkoxyaryl groups can be optionally substituted. Exemplary alkoxyaryl groups include para-anisyl, meta-t-butoxyphenyl, and methylendioxyphenyl.

As used herein, the term "carbon chain of said alkoxy interrupted by a nitrogen atom" refers to a carbon chain of an alkoxy group, wherein a nitrogen atom has been inserted between two adjacent carbon atoms of the carbon chain and wherein alkoxy is as previously defined. Both the alkoxy group and the nitrogen atom can be optionally substituted. Exemplary groups include —OCH$_2$CH$_2$N(CH$_3$)CH$_2$CH$_3$ and —OCH$_2$CH$_2$NHCH$_3$.

As used herein, the term "heterocycloalkylheteroaryl" refers to an heteroaryl group with a heterocycloalkyl substituent wherein heterocycloalkyl and heteroaryl are as previously defined. Heterocycloalkylheteroaryl groups can be optionally substituted. Exemplary heterocycloalkylheteroaryl groups include 3-[N-morpholinyl]pyridine and 3-[2-piperidinyl]pyridine.

As used herein, the term "heteroarylheteroaryl" refers to an heteroaryl group with an heteroaryl substituent wherein heteroaryl is as previously defined. Heteroarylheteroaryl groups can be optionally substituted. Exemplary heteroarylheteroaryl groups include 4-[3-pyridyl]pyridine and 2-[2-quinolyl]quinuclidine.

As used herein, the term "aralkoxyaryl" refers to an aryl group with an aralkoxy substituent wherein aralkoxy and aryl are as previously defined. Aralkoxyaryl groups can be optionally substituted. Exemplary aralkoxyaryl groups include benzyloxyphenyl and meta-toluenyloxyphenyl.

As used herein, the term "arylheteroaryl" refers to an heteroaryl group with an aryl substituent wherein aryl and heteroaryl are as previously defined. Arylheteroaryl groups can be optionally substituted. Exemplary arylheteroaryl groups include 3-phenylpyridyl and 2-naphthalenylquinolinyl.

As used herein, the term "alkoxyheteroaryl" refers to an heteroaryl group with an alkoxy substituent wherein alkoxy and heteroaryl are as previously defined. Alkoxyheteroaryl groups can be optionally substituted. Exemplary alkoxyheteroaryl groups include 2-methoxypyridine and 6-n-propoxyquinoline.

As used herein, "bicycloalkyl" refers to an optionally substituted, alkyl group having two bridged rings in its structure and having from about 7 to about 20 carbon atoms (and all combinations and subcombinations of ranges and specific numbers of carbon atoms therein), with from about 7 to about 15 carbon atoms being preferred. Exemplary bicycloalkyl-ring structures include, but are not limited to, norbornyl, bornyl, [2.2.2]-bicyclooctyl, cis-pinanyl, trans-pinanyl, camphanyl, iso-bornyl, and fenchyl.

As used herein, "bicycloalkenyl" refers to an optionally substituted, alkenyl group having two bridged rings in its structure and having from about 7 to about 20 carbon atoms (and all combinations and subcombinations of ranges and specific numbers of carbon atoms therein), with from about 7 to about 15 carbon atoms being preferred. Exemplary bicycloalkenyl-ring structures include, but are not limited to, bicyclo[2.2.1]hept-5-en-2-yl, bornenyl, [2.2.2]-bicyclooct-5-en-2-yl, alpha-pinenyl, beta-pinenyl, camphenyl, and fenchyl.

As used herein, "carboxy" refers to a —C(=O)OH group.

As used herein, "alkanoyl" refers to a —C(=O)-alkyl group, wherein alkyl is as previously defined. Exemplary alkanoyl groups include acetyl (ethanoyl), n-propanoyl, n-butanoyl, 2-methylpropanoyl, n-pentanoyl, 2-methylbutanoyl, 3-methylbutanoyl, 2,2-dimethylpropanoyl, heptanoyl, and decanoyl.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), carboxyl (—COOH), —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", NR"S(=O)$_2$R", CF$_3$, CF$_2$CF$_3$, NHC(=O)NHR", NHC(=O)NR"R", NR"C(=O)NHR", NR"C(=O)NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

"Side effect" refers to a consequence other than the one(s) for which an agent or measure is used, as the adverse effects produced by a drug, especially on a tissue or organ system other then the one sought to be benefited by its administration.

In the case, for example, of opioids, the term "side effect" may refer to such conditions as, for example, constipation, nausea and/or vomiting.

"Effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount", when used in connection with opioids, for example, for the treatment of pain, refers to the treatment and/or prevention of the painful condition. The term "effective amount", when used in connection with opioid antagonist compounds, refers to the treatment and/or prevention of side effects typically associated with opioids including, for example, such side effects as constipation, nausea and/or vomiting, as well as other side effects, discussed in further detail below.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"In combination with", "combination therapy" and "combination products" refer, in certain embodiments, to the concurrent administration to a patient of opioids and the compounds of formula (I). When administered in combination, each component may be administered at the same time or sequentially in any order at different points in time. Thus, each component may be administered separately but sufficiently closely in time so as to provide the desired therapeutic effect.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

"Patient" refers to animals, including mammals, preferably humans.

"Prodrug" refers to compounds specifically designed to maximize the amount of active species that reaches the desired site of reaction which are of themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

The piperidines of the invention as illustrated in formula I can occur as the trans and cis stereochemical isomers at the 3- and 4-positions of the piperidine ring. The term "trans" as used herein refers to the $R^2$ substituent being on the opposite side of the $R^3$ substituent, whereas in the "cis" isomer, the $R^2$ substituent and the $R^3$ substituent are on the same side of the ring. The present invention contemplates the individual stereoisomers, as well as racemic mixtures. In the most preferred compounds of the present invention, the $R^2$ substituent and the $R^3$ substituent are in the "trans" orientation on the piperidine.

In addition to the "cis" and trans" orientation of the $R^2$ substituent and the $R^3$ substituent, the absolute stereochemistry of the carbon atoms bearing the $R^2$ substituent and the $R^3$ substituent is also defined as using the commonly employed "R" and "S" definitions (Orchin et al., *The Vocabulary of Organic Chemistry*, John Wiley and Sons, Inc., page 126, which is incorporated herein by reference). The preferred compounds of the present invention are those of formula I in which the configuration of both the $R^2$ substituent and the $R^3$ substituent on the piperidine ring is "R".

Furthermore, asymmetric carbon atoms may be introduced into the molecule depending on the structure of $R^4$. As such, these classes of compounds can exist as the individual "R" or "S" stereoisomers at these chiral centers, or the racemic mixture of the isomers, and all are contemplated as within the scope of the present invention. Preferably, a substantially pure stereoisomer of the compounds of this invention is used, i.e., an isomer in which the configuration at the chiral center is "R" or "S", i.e., those compounds in which the configuration at the three chiral centers I preferably 3R, 4R, 5 or 3R, 4R, R.

In certain preferred embodiments, the compounds, pharmaceutical compositions and methods of the present invention may involve a peripheral opioid antagonist compound. The term "peripheral" designates that the compound acts primarily on physiological systems and components external to the central nervous system. In preferred form, the peripheral opioid antagonist compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5% and most preferably 0% of the pharmacological activity of the compounds employed in the present methods is exhibited in the CNS.

Furthermore, it is preferred in certain embodiments of the invention where the compound is administered to antagonize the peripheral side effects of an opioid that the compound does not substantially cross the blood-brain barrier and thereby decrease the beneficial activity of the opioid. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following i.v. administration.

Accordingly, in one embodiment, the present invention provides novel pharmaceutically active compounds of formula I:

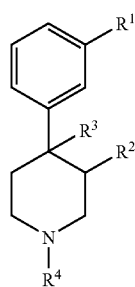

I wherein:
  $R^1$ is —C(=O)OR$^5$, —C(=O)NR$^6$R$^7$, —NR$^6$R$^7$, or —CH$_2$OR$^5$;
  $R^2$ and $R^3$ are each independently alkyl or alkenyl;
  $R^4$ is
    H,
    cycloalkyl,
    heterocycloalkyl, or
    $C_{1-10}$ alkyl which is substituted with at least one:
      substituted aryl, wherein at least one of said aryl substituents is other than OH, nitro, amino, halo, CN, CH$_2$CN, CONH$_2$, $C_{1-4}$ alkyl, $C_{1-4}$ alkoxy, or $C_{1-5}$ alkanoyl (which latter three groups are optionally substituted by one or more halo atoms),
      aryloxyaryl,
      -aryl-N(H)R$^b$,
      -aryl-N(R$^b$)R$^b$,
      heteroarylaryl,
      alkoxyaryl, wherein the carbon chain of said alkoxy is interrupted by a nitrogen atom,
      substituted alkoxyaryl, provided that when one or more substituents are present on the alkoxy group, at least one of said substituents is other than halo,
      substituted cycloalkyl,
      RS(=O)$_p$ substituted heteroaryl,
      RS(=O)$_p$ substituted heterocycloalkyl,
      RS(=O)$_p$ substituted aryl,
      heterocycloalkylheteroaryl,
      heteroarylheteroaryl,
      bicycloalkyl,
      bicycloalkenyl,
      carboxy,
      —CO$_2$R$^a$,
      —C(=O)N(R$^{6a}$)—R$^{6b}$—CO$_2$H,
      —C(=O)N(R$^{6a}$)—R$^{6a}$—CO$_2$R,
      —C(=O)N(R$^{6a}$)—R$^{6a}$—C(=O)NR$^{7a}$R$^{7b}$,
      —N(R$^{7c}$)C(=O)R$^{7d}$,
      —N(R$^{7c}$)S(=O)$_2$R$^{7d}$,
      aralkoxyaryl,
      substituted arylheteroaryl, or
      substituted alkoxyheteroaryl, provided that when one or more substituents are present on the alkoxy group, at least one of said substituents is other than halo;
  p is 0, 1, or 2;
  R is alkyl, aralkyl, or aryl;
  $R^a$ is H, alkyl, alkenyl, cycloalkyl, aryl, or heteroaryl, provided that $R^a$ is not $C_{1-6}$ alkyl;
  each $R^b$ is independently alkyl, cycloalkyl, aralkyl, or aryl,
  $R^{6a}$ is H, alkyl, aralkyl, cycloalkyl, alkenyl, aryl, heteroaralkyl, or heteroaryl;
  $R^{6b}$ is lower alkylene, or lower aralkylene or, together with the nitrogen atom to which they are attached, $R^{6a}$ and $R^{6b}$ form a 4- to 7-membered heterocycloalkyl ring;
  $R^{7a}$ and $R^{7b}$ are each independently H, alkyl, cycloalkyl, heterocycloalkyl, heteroaryl, aralkyl, or aryl or, together with the nitrogen atom to which they are attached, $R^{7a}$ and $R^{7b}$ form a 4- to 7-membered heterocycloalkyl ring, provided that at least one of $R^{1a}$ and $R^{7b}$ is other than H;
  $R^{7c}$ and $R^{7d}$ are each independently H, alkyl, cycloalkyl, heterocycloalkyl, heteroaryl, aralkyl, or aryl;
  $R^5$ is H or alkyl; and
  each $R^6$ and $R^7$ is independently H, alkyl, or —C(=O)R, or together with the nitrogen atom to which they are attached, $R^6$ and $R^7$ form a 4- to 7-membered heterocycloalkyl ring, provided that no more than one of $R^6$ and $R^7$ is —C(=O)R, and provided that when $R^1$ is NR$^6$R$^7$, $R^4$ can also be aralkyl;

or a stereoisomer, prodrug, pharmaceutically acceptable salt, hydrate, solvate, acid salt hydrate, N-oxide or isomorphic crystalline form thereof, provided that $R^2$ and $R^3$ are not in the cis stereoisomer conformation when both $R^2$ and $R^3$ are methyl.

In certain preferred embodiments, $R^1$ is —C(=O)OR$^5$, —C(=O)NR$^6$R$^7$, or —NR$^6$R$^7$.

Also in the above compounds of formula I, $R^2$ and $R^3$ are each independently alkyl or alkenyl. Preferably, $R^2$ and $R^3$ are each independently alkyl. Even more preferably, $R^2$ and $R^3$ are methyl.

Also in the above compounds of formula I, preferably, $R^4$ is:
H,
cycloalkyl,
heterocycloalkyl, or
$C_{1-10}$ alkyl which is substituted with at least one:
    substituted aryl, wherein said aryl substituent is other than OH, nitro, amino, halo, CN, CH$_2$CN, CONH$_2$, $C_{1-4}$ alkyl, $C_{1-4}$ alkoxy, or $C_{1-5}$ alkanoyl (which latter three groups are optionally substituted by one or more halo atoms),
    aryloxyaryl,
    -aryl-N(H)R$^b$,
    heteroarylaryl,
    alkoxyaryl, wherein the carbon chain of said alkoxy is interrupted by a nitrogen atom,
    substituted alkoxyaryl, provided that when one or more substituents are present on the alkoxy group, at least one of said substituents is other than halo,
    substituted cycloalkyl,
    RS(=O)$_p$ substituted heteroaryl,
    RS(=O)$_p$ substituted heterocycloalkyl,
    RS(=O)$_p$ substituted aryl,
    heterocycloalkylheteroaryl,
    heteroarylheteroaryl,
    bicycloalkyl,
    bicycloalkenyl,
    carboxy,
    —CO$_2$R$^a$,
    —C(=O)N(R$^{6a}$)—R$^{6b}$—CO$_2$H,
    —C(=O)N(R$^{6a}$)—R$^{6b}$—CO$_2$R,
    —C(=O)N(R$^{6a}$)—R$^{6b}$—C(=O)NR$^{7a}$R$^{7b}$,
    —N(R$^{7c}$)C(=O)R$^{7d}$,
    —N(R$^{7c}$)S(=O)$_2$R$^{7d}$,
    aralkoxyaryl,
    substituted arylheteroaryl, or
    substituted alkoxyheteroaryl, provided that when one or more substituents are present on the alkoxy group, at least one of said substituents is other than halo.
Even more preferably, $R^4$ is:
H,
cycloalkyl,
heterocycloalkyl, or
$C_{1-10}$ alkyl which is substituted with at least one:
    aryloxyaryl,
    -aryl-N(H)R$^b$,
    -aryl-N(R$^b$)R$^b$,
    heteroarylaryl,
    alkoxyaryl, wherein the carbon chain of said alkoxy is interrupted by a nitrogen atom,
    substituted cycloalkyl,
    RS(=O)$_p$ substituted heteroaryl,
    RS(=O)$_p$ substituted heterocycloalkyl,
    RS(=O)$_p$ substituted aryl,
    heterocycloalkylheteroaryl,
    heteroarylheteroaryl,
    bicycloalkyl,
    bicycloalkenyl,
    carboxy,
    —CO$_2$R$^a$,
    —C(=O)N(R$^{6a}$)—R$^{6b}$—CO$_2$H,
    —C(=O)N(R$^{6a}$)—R$^{6b}$—CO$_2$R,
    —C(=O)N(R$^{6a}$)—R$^{6b}$—C(=O)NR$^{7a}$R$^{7b}$,
    —N(R$^{7c}$)C(=O)R$^{7d}$,
    aralkoxyaryl, or
    substituted arylheteroaryl.

Most preferably, $R^4$ is —(CH$_2$)$_n$—CH(R$^8$)—C(=O)OR$^9$, —(CH$_2$)$_n$—CH(R$^8$)—C(=O)NR$^{10}$NR$^{11}$, or —(CH$_2$)$_n$—CH(R$^8$)—(CH$_2$)$_m$—NR$^{19}$R$^{20}$.

In certain preferred embodiments of the compounds of formula I, $R^4$ is

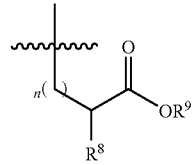

wherein:
$R^8$ is alkyl, aralkyl, cycloalkyl, alkylcycloalkyl, aryl, heteroaryl, or heteroaralkyl;
$R^9$ is H, alkyl, alkenyl, cycloalkyl, aryl, or heteroaryl; and n is an integer from 1 to 3;
provided that $R^9$ is not $C_{1-6}$ alkyl.

In certain other preferred embodiments of the compounds of formula I, $R^4$ is

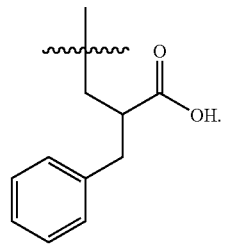

In yet other preferred embodiments of the compounds of formula I, $R^4$ is

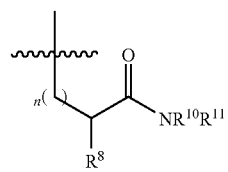

wherein:
$R^8$ is alkyl, aralkyl, cycloalkyl, alkylcycloalkyl, aryl, heteroaryl, or heteroaralkyl;
$R^{10}$ is —R$^{6b}$—CO$_2$H, —R$^{6b}$—CO$_2$R$^{10a}$, or —R$^{6b}$—C(=O)NR$^{10b}$R$^{10c}$;
$R^{11}$ is H, alkyl, alkenyl, cycloalkyl, aryl, aralkyl, heteroaralkyl or heteroaryl, or together with the nitrogen atom to which they are attached, $R^{6b}$ and $R^{11}$ form a 4- to 7-membered heterocycloalkyl ring, or;
$R^{10a}$ is alkyl or aralkyl;

$R^{10b}$ and $R^{10c}$ are each independently H or alkyl, or together with the nitrogen atom to which they are attached, $R^{10b}$ and $R^{10c}$ form a 4- to 7-membered heterocycloalkyl ring, provided that at least one of $R^{10b}$ and $R^{10c}$ is other than H; and n is an integer from 1 to 3.

In other preferred embodiments of the compounds of formula I, $R^4$ is

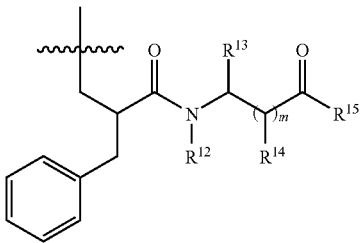

wherein:
$R^{12}$ is H, lower alkyl, or aralkyl;
$R^{13}$ is H, alkyl, cycloalkyl, or aryl, or together with the nitrogen and carbon atoms to which they are respectively attached, $R^{12}$ and $R^{13}$ form a 4- to 7-membered heterocycloalkyl ring;
each $R^{14}$ independently is H, alkyl, cycloalkyl or aryl;
$R^{15}$ is —$OR^{16}$ or —$NR^{17}R^{18}$;
$R^{16}$, $R^{17}$, and $R^{18}$ are each, independently H, or alkyl or, together with the nitrogen atom to which they are attached, $R^{17}$ and $R^{18}$ form a 4- to 7-membered heterocycloalkyl ring; and
m is an integer from 0 to 3;
provided that at least one of $R^{17}$ and $R^{18}$ is other than H.

In still other preferred embodiments of the compounds of formula I, $R^4$ is

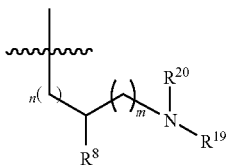

wherein:
$R^8$ is alkyl, aralkyl, cycloalkyl, alkylcycloalkyl, or aryl;
$R^{19}$ is H, alkyl, cycloalkyl, or aryl;
$R^{20}$ is —$C(=O)R^{21}$, or —$S(=O)_2R^{21}$;
$R^{21}$ is alkyl, cycloalkyl, heterocycloalkyl, aralkyl, aryl, or heteroaryl;
m is an integer from 0 to 3; and
n is an integer from 1 to 3.

In other preferred embodiments of the compounds of formula I, $R^4$ is

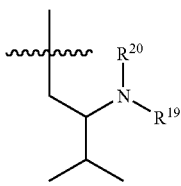

wherein:
$R^{19}$ is H or alkyl.

In the above compounds of formula I, $R^5$ is H or alkyl.

Also in the above compounds of formula I, $R^6$ and $R^7$ are each independently H, alkyl, or —$C(=O)R$, or together with the nitrogen atom to which they are attached, $R^6$ and $R^7$ form a 4- to 7-membered heterocycloalkyl ring, provided that no more than one of $R^6$ and $R^7$ is —$C(=O)R$, and provided that when $R^1$ is —$NR^6R^7$, $R^4$ can also be aralkyl.

In yet other preferred embodiments of the compounds of formula I, $R^1$ is —$C(=O)OR^5$, —$C(=O)NR^6R^7$; or —$NR^6R^7$, and $R^4$ is $C_{1-10}$ alkyl, which is substituted with —$N(R^{7c})C(=O)R^{7d}$, —$C(=O)N(R^{6a})$—$R^{6b}$—$CO_2H$, or —$C(=O)N(R^{6a})$—$R^{6b}$—$CO_2R$. More preferably, $R^4$, $R^5$, and $R^6$ are H.

The above compounds of formula I also include but are not limited to other forms, such as their stereoisomers, prodrugs, pharmaceutically acceptable salt, hydrate, solvate, acid salt hydrate, N-oxide or isomorphic crystalline form thereof, provided that $R^2$ and $R^3$ are not in the cis stereoisomer conformation when both $R^2$ and $R^3$ are methyl.

In a more preferred embodiment of the present invention, there are provided compounds of the formula I which have the following formula Ia:

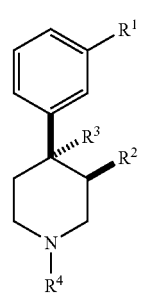

Ia

More preferably, the compounds of formula Ia have the following formula IIa:

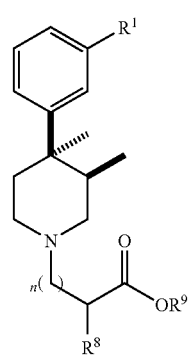

IIa wherein:
$R^8$ is alkyl, aralkyl, cycloalkyl, alkylcycloalkyl, aryl, heteroaryl, or heteroaralkyl;
$R^9$ is H, alkyl, alkenyl, cycloalkyl, aryl, or heteroaryl; and
n is an integer from 1 to 3;
provided that $R^9$ is not $C_{1-6}$ alkyl.

In the above compounds of formula IIa, $R^8$ is alkyl, aralkyl, cycloalkyl, alkylcycloalkyl, aryl, heteroaryl, or heteroaralkyl.

Preferably, $R^8$ is aralkyl, and $R^9$ is H or alkyl, provided that $R^9$ is not $C_{1-6}$ alkyl. More preferably, the compounds of the formula IIa have the following formula IIIa:

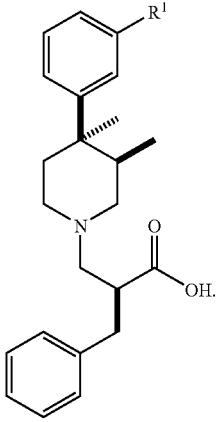

IIIa

In another more preferred embodiment of the present invention, there are provided compounds of the formula Ia which have the following formula IVa:

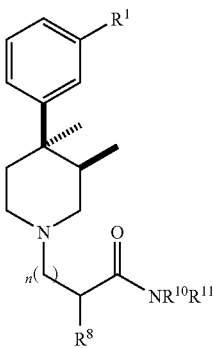

IVa wherein:
- $R^8$ is alkyl, aralkyl, cycloalkyl, alkylcycloalkyl, aryl, heteroaryl, or heteroaralkyl;
- $R^{10}$ is —$R^{6b}$—$CO_2H$, —$R^{6b}$—$CO_2R^{10a}$, or —$R^{6b}$—C(=O)$NR^{10b}R^{10c}$;
- $R^{11}$ is H, alkyl, alkenyl, cycloalkyl, aryl, aralkyl, heteroaralkyl or heteroaryl, or together with the nitrogen atom to which they are attached, $R^{6b}$ and $R^{11}$ form a 4- to 7-membered heterocycloalkyl ring;
- $R^{10a}$ is alkyl or aralkyl;
- $R^{10b}$ and $R^{10c}$ are each independently H or alkyl, or together with the nitrogen atom to which they are attached, $R^{10b}$ and $R^{10c}$ form a 4- to 7-membered heterocycloalkyl ring, provided that at least one of $R^{10b}$ and $R^{10c}$ is other than H; and
- n is an integer from 1 to 3.

In the above compounds of formula IVa, preferably $R^8$ is aralkyl. More preferably, $R^8$ is benzyl, and n is 1. More preferably, the compounds of formula IVa have the following formula Va:

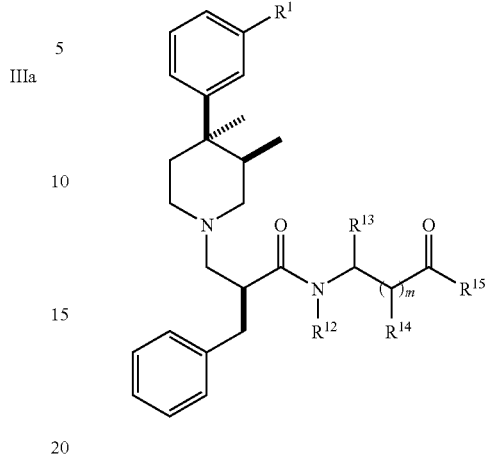

Va wherein:
- $R^{12}$ is H, lower alkyl, or aralkyl;
- $R^{13}$ is H, alkyl, cycloalkyl, or aryl, or together with the nitrogen and carbon atoms to which they are respectively attached, $R^{12}$ and $R^{13}$ form a 4- to 7-membered heterocycloalkyl ring;
- each $R^{14}$ independently is H, alkyl, cycloalkyl or aryl;
- $R^{15}$ is —$OR^{16}$ or —$NR^{17}R^{18}$;
- $R^{16}$, $R^{17}$, and $R^{18}$ are each, independently H, or alkyl or, together with the nitrogen atom to which they are attached, $R^{17}$ and $R^{18}$ form a 4- to 7-membered heterocycloalkyl ring; and
- m is an integer from 0 to 3;
- provided that at least one of $R^{17}$ and $R^{18}$ is other than H.

In another more preferred embodiment of the present invention, there are provided compounds of the formula Ia which have the following formula VIa:

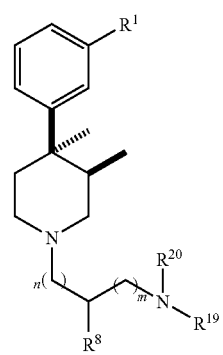

VIa wherein:
- $R^8$ is alkyl, aralkyl, cycloalkyl, alkylcycloalkyl, or aryl;
- $R^{19}$ is H, alkyl, cycloalkyl, or aryl;
- $R^{20}$ is —$C(O)R^{21}$, or —$S(=O)_2R^{21}$;
- $R^{21}$ is alkyl, cycloalkyl, heterocycloalkyl, aralkyl, aryl, or heteroaryl;
- m is an integer from 0 to 3; and
- n is an integer from 1 to 3.

In the above compounds of formula VIa, preferably $R^8$ is alkyl. More preferably $R^8$ is isopropyl and $R^{19}$ is H or alkyl. Even more preferably, n is 1. Most preferably, the compounds of formula VIa have the following formula VIIIa:

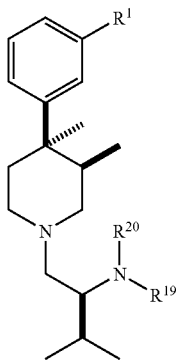

VIIa wherein:

$R^{19}$ is H or alkyl.

In certain preferred embodiments of the compound of formula I, $R^1$ is —C(O)OR$^5$, —C(O)NR$^6$R$^7$ or —NR$^6$R$^7$; and $R^4$ is $C_{1-10}$ alkyl, which is substituted with —N(R$^{7c}$)C(=O)R$^{7d}$, —C(=O)N(R$^{6a}$)—R$^{6b}$—CO$_2$H, or —C(=O)N(R$^{6a}$)—R$^{6b}$—CO$_2$R. More preferably, R$^4$ is $C_{1-10}$ alkyl, which is substituted with —N(R$^{7c}$)C(=O)R$^{7d}$. Even more preferably, when R$^4$ is $C_{1-10}$ alkyl, which is substituted with —N(R$^{7c}$)C(=O)R$^{7d}$, R$^5$, R$^6$, and R$^7$ are H.

In other more preferred embodiments of the compound of formula I, $R^1$ is —C(O)OR$^5$, —C(O)NR$^6$R$^7$ or —NR$^6$R$^7$; and $R^4$ is $C_{1-10}$ alkyl, which is substituted with —C(=O)N(R$^{6a}$)—R$^{6b}$—CO$_2$H. Even more preferably, when R$^4$ is $C_{1-10}$ alkyl, which is substituted with —C(=O)N(R$^{6a}$)—R$^{6b}$—CO$_2$H, R$^5$, R$^6$, and R$^7$ are H.

In still other more preferred embodiments of the compound of formula I, $R^1$ is —C(O)O R$^5$, —C(=O)NR$^6$R$^7$ or —NR$^6$R$^7$; and $R^4$ is $C_{1-10}$ alkyl, which is substituted with —C(=O)N(R$^{6a}$)—R$^{6b}$—CO$_2$R. Even more preferably, when R$^4$ is $C_{1-10}$ alkyl, which is substituted with —C(=O)N(R$^{6a}$)—R$^{6b}$—CO$_2$R, R$^5$, R$^6$, and R$^7$ are H.

In certain preferred embodiments of the compound of formula Ia, $R^1$ is —C(=O)O R$^5$, —C(=O)NR$^6$R$^7$ or —NR$^6$R$^7$; and $R^2$ and $R^3$ are methyl, and $R^4$ is $C_{1-10}$ alkyl, which is substituted with —, N(R$^{7c}$)C(=O)R$^{7d}$—C(=O)N(R$^{6a}$)—R$^{6b}$—CO$_2$H, or —C(=O)N(R$^{6a}$)—R$^{6b}$—CO$_2$R. More preferably, R$^4$ is $C_{1-10}$ alkyl, which is substituted with —N(R$^{7c}$)C(=O)R$^{7d}$. Even more preferably, when R$^4$ is $C_{1-10}$ alkyl, which is substituted with —N(R$^{7c}$)C(=O)R$^{7d}$R$^5$, R$^6$, and R$^7$ are H.

In other preferred embodiments of the compound of formula Ia, $R^1$ is —C(=O)O R$^5$, —C(=O)NR$^6$R$^7$ or —NR$^6$R$^7$; and $R^2$ and $R^3$ are methyl; and $R^4$ is $C_{1-10}$ alkyl, which is substituted with —C(=O)N(R$^{6a}$)—R$^{6b}$—CO$_2$H. Even more preferably, when R$^4$ is $C_{1-10}$ alkyl, which is substituted with —C(=O)N(R$^{6a}$)—R$^{6b}$—CO$_2$H, R$^5$, R$^6$, and R$^7$ are H.

In still other preferred embodiments of the compound of formula Ia, $R^1$ is —C(=O)O R$^5$, —C(=O)NR$^6$R$^7$ or —NR$^6$R$^7$; and $R^2$ and $R^3$ are methyl; and $R^4$ is $C_{1-10}$ alkyl, which is substituted with —C(=O)N(R$^{6a}$)—R$^{6b}$—CO$_2$R. Even more preferably, when R$^4$ is $C_{1-10}$ alkyl, which is substituted with —C(=O)N(R$^{6a}$)—R$^{6b}$—CO$_2$R, R$^5$, R$^6$, and R$^7$ are H.

The compounds employed in the methods of the present invention may exist in prodrug form. As used herein, "prodrug" is intended to include any covalently bonded carriers which release the active parent drug, for example, as according to formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, isopropyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The 3,4-disubstituted-4-aryl piperidine compounds according to the present invention may be synthesized employing methods taught, for example, in U.S. Pat. Nos. 5,250,542, 5,434,171, 5,159,081, and 5,270,328, the disclosures of which are hereby incorporated herein by reference in their entireties. The optically active (+)-4(R)-(3-hydroxyphenyl)-3(R),4-dimethyl-1-piperidine was employed as starting material in the synthesis of the present compounds may be prepared by the general procedure taught in *J. Org. Chem.,* 1991, 56, 1660-1663, U.S. Pat. No. 4,115,400 and U.S. Pat. No. 4,891,379, the disclosures of which are hereby incorporated herein by reference in their entireties.

While not intending to be bound by any theory or theories of operation, it is contemplated that opioid side effects, such as constipation, vomiting and nausea, may result from undesirable interaction of the opioid with peripheral opioid receptors, such as peripheral μ receptors. Administration of the compounds of formula I according to one aspect of the present invention may block interaction of the opioid compounds with the peripheral receptors, thereby preventing and/or inhibiting the side effects, while preferably not interfering with the therapeutic effect of the opioid in the CNS.

In accordance with certain embodiments of the present invention, there are provided methods which comprise administering to a patient, inter alia, an opioid compound. A wide variety of opioids are available which may be suitable for use in the present methods and compositions. Generally speaking, it is only necessary that the opioid provide the desired effect (for example, pain alleviation), and be capable of being incorporated into the present combination products and methods (discussed in detail below). In preferred embodiments, the present methods and compositions may involve an opioid which is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil and/or tramadol. More preferably, the opioid is selected from morphine, codeine, oxycodone, hydrocodone, dihydrocodeine, propoxyphene, fentanyl and/or tramadol.

The opioid component of the present compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J. et al., *Pain* 1996, 67, 361), L-364,718 and other CCK antagonists (Dourish, C. T. et al., *Eur J Pharmacol* 1988, 147, 469), NOS inhibitors (Bhargava, H. N. et al., *Neuropeptides* 1996, 30, 219), PKC inhibitors (Bilsky, E. J. et al., *J Pharmacol Exp Ther* 1996, 277, 484), and dynorphin antagonists or antisera (Nichols, M. L. et al., *Pain* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Another embodiment of the invention provides a pharmaceutical composition comprising a pharmaceutically acceptable carrier and an effective amount of a compound of formula I.

Yet another embodiment of the invention provides a method for treating or preventing opioid-bowel dysfunction comprising the step of administering to a patient in need of such treatment a composition comprising an opioid and an effective amount of a compound of formula I.

Still another embodiment of the invention provides a method for treating or preventing ileus comprising the step of administering to a patient in need of such treatment, an effective amount of a compound of formula I.

Another embodiment of the invention provides a method for treating or preventing a side effect associated with an opioid comprising the step of administering to a patient, an effective amount of a compound of formula I.

Although the compounds of the present invention may be administered as the pure chemicals, it is preferable to present the active ingredient as a pharmaceutical composition.

The invention thus further provides a pharmaceutical composition comprising one or more of the compounds of formula I, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

The compounds of the invention may be administered in an effective amount by any of the conventional techniques well-established in the medical field. The compounds employed in the methods of the present invention including, for example, opioid and the compounds of formula I, may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entirety.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The combination products of this invention, such as pharmaceutical compositions comprising opioids in combination with the compounds of formula I, may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the opioid compounds and the compounds of formula I may be administered at the same time (that is, together), or in any order. When not administered at the same time, preferably the administration of an opioid and the compounds of formula I occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the opioids and the compounds of formula I are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where an opioid compounds is combined with the compounds of formula I, for example, typically a daily dosage may range from about 0.01 to about 100 milligrams of the opioid (and all combinations and subcombinations of ranges therein) and about 0.001 to about 100 milligrams of the compounds of formula I (and all combinations and subcombinations of ranges therein), per kilogram of patient body weight. Preferably, the a daily dosage may be about 0.1 to about 10 milligrams of the opioid and about 0.01 to about 10 milligrams of the compounds of formula I per kilogram of patient body weight. Even more preferably, the daily dosage may be about 1.0 milligrams of the opioid and about 0.1 milligrams of the compounds of formula I per kilogram of patient body weight. With regard to a typical dosage form of this type of combination product, such as a tablet, the opioid compounds (e.g., morphine) generally may be present in an amount of about 15 to about 200 milligrams, and the compounds of formula I in an amount of about 0.1 to about 4 milligrams.

Particularly when provided as a single dosage form, the potential exists for a chemical interaction between the combined active ingredients (for example, an opioid and the compounds of formula I). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the treatment of pain, which comprise a therapeutically effective amount of an opioid along with a therapeutically effective amount of the 3,4-disubstituted-4-aryl-piperidine compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The opioid compound and the compounds of formula I may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

The compounds of the present invention may be used in methods to bind opioid receptors, including μ and κ opioid receptors. Such binding may be accomplished by contacting the receptor with an effective amount of the compound of the invention. Preferably, the contacting step conducted in an aqueous medium, preferably at physiologically relevant ionic strength, pH, and the like.

In certain preferred embodiments, the compounds of the present invention bind μ and κ opioid receptors or combinations thereof. The opioid receptors may be located in the central nervous system or located peripherally to the central nervous system or in both locations.

In certain other preferred embodiments, the compounds of the present invention bind K opioid receptors.

In preferred embodiments of the methods of the invention, the compounds antagonize the activity of the opioid receptors. In other preferred embodiments, the compounds prevent or treat a condition or disease caused by an opioid (either endogenous or exogenous). In certain embodiments of the method, particularly where the opioid are exogenous, the compounds of the invention preferably do not substantially cross the blood-brain barrier.

The compounds of the present invention may be used in methods to antagonize µ, κ or both types of opioid receptors, particularly where undesirable symptoms or conditions are side effects of administering exogenous opioids. Furthermore, the compounds of the invention may be used as to treat patients having disease states that are ameliorated by binding opioid receptors or in any treatment wherein temporary suppression of the µ, κ or both types of opioid receptor system is desired.

Such symptoms, conditions or diseases include the complete or partial antagonism of opioid-induced sedation, confusion, respiratory depression, euphoria, dysphoria, hallucinations, pruritus (itching), increased biliary tone, increased biliary colic, and urinary retention, ileus, emesis, and addiction liability; prevention or treatment of opioid and cocaine dependence; rapid opioid detoxification; treatment of alcoholism; treatment of alcoholic coma; detection of opioid use or abuse (pupil test); treatment of eating disorders; treatment of obesity; treatment of post-concussional syndrome; adjunctive therapy in septic, hypovolemic or endotoxin-induced shock; potentiation of opioid analgesia (especially at ultra-low doses); reversal or prevention of opioid tolerance and physical dependence (especially at ultra-low doses); prevention of sudden infant death syndrome; treatment of psychosis (especially wherein the symptoms are associated with schizophrenia, schizophreniform disorder, schizoaffective disorder, unipolar disorder, bipolar disorder, psychotic depression, Alzheimer's disease, Parkinson's disease, compulsive disorders, and other psychiatric or neurologic disorders with psychosis as symptoms); treatment of dyskinesia, treatment of autism; treatment of the endocrine system (including increased release of leutinizing hormone, treatment of infertility, increasing number of multiple births in animal husbandry, and male and female sexual behavior); treatment of the immune system and cancers associated with binding of the opioid receptors; treatment of anxiolysis; treatment of diuresis; treatment and regulation of blood pressure; treatment of tinnitus or impaired hearing; treatment of epilepsy; treatment of cachexia; treatment of general cognitive dysfunctions; and treatment of kleptomania.

The compounds of the invention present invention may also be used as cytostatic agents, as antimigraine agents, as immunomodulators, as immunosuppressives, as antiarthritic agents, as antiallergic agents, as virucides, to treat diarrhea, antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds may be used in the treatment of Parkinson" disease as an adjunct to L-dopa for treatment dyskinesia associated with the L-dopa treatment.

In certain preferred embodiments, the compounds of the invention may be used in methods for preventing or treating gastrointestinal dysfunction, including, but not limited to, irritable bowel syndrome, opioid-bowel dysfunction, colitis, post-operative and opioid-induced emesis (nausea and vomiting), decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

In certain preferred embodiments, the compounds of the invention may be used in methods for preventing or treating post-operative or opioid-induced ileus.

In other preferred embodiments, the compounds of the invention may be used in an effective amount in a method in combination with an effective amount of an opioid to treat pain.

The compounds of the invention may be administered before, during or after administering at least one opioid. The methods of the invention are particularly effective for opioids selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

A series of N-substituted (+)-4(R)-(3-substituted phenyl)-3(R),4-dimethyl-1-piperidine derivatives (Formula I) were prepared according to the Schemes 1-9. The derivatives of formula I ($R^1$ is $COOR^5$) were prepared according to the Schemes 1-4.

The key intermediate 7 used as starting material for the solid phase synthesis of compounds of Formula I ($R^1$ is $CONH_2$, $COOR^5$) was prepared in 6 steps from (+)-4(R)-(3-hydroxyphenyl)-3(R),4-dimethyl-1-piperidine (1) (Scheme 1). Condensation of 1 (J. Org. Chem., 1991, 56, 1660-1663) with tert-butyloxycarbonylanhydride afforded the tert-butyloxycarbonyl (Boc)-protected derivative 2 which was converted to the triflate 3 using N-phenyltrifluoromethane sulfonimide in a halogenated solvent such as dichloromethane and a tertiary amine base such as triethylamine. Palladium catalyzed carbonylation of 3 afforded the methyl ester 4 which was converted to the secondary amine 5 by acidic cleavage of the Boc protecting group. Acidic cleavage conditions include solutions of trifluoroacetic acid in a halogenated solvent at room temperature or as in this case, a solution of anhydrous HCl in methanol. Condensation of 5 with 2-(trimethylsilyl)ethyl p-nitrophenylcarbonate (Fluka Chemical Company) afforded the corresponding 2-(trimethylsilyl)ethylcarbamate or TeOC derivative 6 which was hydrolyzed under basic conditions to give the carboxylic acid 7.

Coupling of the acid 7 with the Wang resin afforded the resin 8 which was converted to the resin 9 by treatment with tetrabutylammonium fluoride (Scheme 2). Reductive aminations were conducted using aldehydes or ketones and borane/pyridine to give the resin-bound N-substituted derivatives 11. A wide range of aldehydes and ketones were employed in the reductive amination reaction. For those aldehydes and ketones that contained a basic nitrogen atom, such compounds were protected as there BOC derivatives (e.g., N-Boc-4-piperidinone). Cleavage of the resin using trifluoroacetic acid gave the desired carboxylic acid derivatives (Formula I; $R^5$ is H). Alternatively, cleavage of resin 11 with alcohols such as methanol, benzyl alcohol, and the like under acidic conditions gave esterified compounds of Formula I ($R^5$ is alkyl). Under the acidic cleavage conditions, all Boc protecting groups were simultaneously removed to generate the corresponding primary or secondary amine. The purity of cleaved products was generally >50% as determined by LCMS and compounds could be purified to >98% purity by routine HPLC.

In addition to the solid-phase synthesis of compounds of Formula I, standard solution-phase synthesis was also conducted. For example, the synthetic route employed for the preparation of the carboxylic acid 17b is outlined in Scheme 3. Coupling of the acid 13 [Werner et al. *J. Org. Chem.*, 1996, 61, 587-597] with glycine tert-butyl ester in the presence of dicyclohexylcarbodiimide and hydroxybenzotriazole afforded the tert-butyl ester 14b which was converted to the triflate 15b using N-phenyltrifluoromethane sulfonimide. Palladium catalyzed carbonylation of 15b afforded the diester 16b which was converted to the carboxylic acid 17b by acidic cleavage of the ester protecting group. Preparation of the carboxylic acid 17a from 13 was conducted using a similar procedure as described above. The methyl ester 14a [Werner et al. *J. Org. Chem.*, 1996, 61, 587-597] was converted to the triflate 15a using N-phenyltrifluoromethane sulfonimide. Palladium catalyzed carbonylation of 15a afforded the diester 16a which was converted to the carboxylic acid 17a by basic cleavage of the methyl esters protecting groups.

Compounds of general formula VIIa were synthesized according to the Scheme 4. As an example, oxidation of N-Boc-L-valinol (Aldrich Chemical company) using the Dess Martin periodinane (Lancaster Chemical company) afforded the corresponding N-Boc-L-valinal which was coupled to the piperidine 5 (see Scheme 1) under reductive amination conditions using borane/pyridine as reducing agent. The resulting carbamate 18 was converted to the primary amine 19 (isolated as its dihydrochloride salt) under acidic conditions. Coupling of 19 with 3-(4-hydroxyphenyl)propionic acid (Aldrich Chemical company) using BOP as coupling agent provided the amide 20 which was hydrolyzed under basic conditions to give the carboxylic acid 21. Coupling of 21 with ammonium chloride using EDCI as coupling agent provided the carboxamide 22.

The derivatives of formula I ($R^1$ is $CONR^6R^7$) were prepared according to the Schemes 5-7.

Coupling of the acid 7 (Scheme 1) with the Fmoc-deprotected Rink amide resin afforded the resin 23 which was converted to the resin 24 by treatment with tetrabutylammonium fluoride (Scheme 5). A wide range of aldehydes and ketones were employed in the reductive amination reaction. For those aldehydes and ketones that contained a basic nitrogen atom, such compounds were protected as their Boc derivatives (e.g., N-Boc-4-piperidinone). Cleavage of the resin using trifluoroacetic acid gave the desired carboxamide derivatives (Formula I; $R^1$ is $CONH_2$). Under the acidic cleavage conditions, all Boc protecting groups were simultaneously removed to generate the corresponding primary or secondary amine. The purity of cleaved products was generally >50% as determined by LCMS and compounds could be purified to >98% purity by routine HPLC.

In addition to the solid-phase synthesis of compounds of Formula I ($R^1$ is $CONR^6R^7$), standard solution-phase synthesis was also conducted. For example, the synthetic route employed for the preparation of the carboxamides 29 is outlined in Scheme 6. Palladium catalyzed formation of the carboxamides 28 from the triflates 15 (Scheme 3) was conducted in the presence of carbon monoxide and $(TMS)_2NH$. Acidic hydrolysis of 28 afforded the target compounds 29 as their TFA salt.

The solution-phase synthesis of compounds of Formula I ($R^1$ is $CONR^6R^7$) may also be conducted as described in Scheme 7. Condensation of I with aldehydes or ketones under reductive amination conditions using borane/pyridine as reducing agent affords the derivatives 30 which are converted to the triflates 31 using N-phenyltrifluoromethane sulfonimide in a halogenated solvent such as dichloromethane and a tertiary amine base such as triethylamine. Palladium catalyzed carbonylation of 31 provides the methyl esters 32 which are hydrolyzed under basic conditions to give the carboxylic acids 33. Coupling of 33 with various amines affords the primary, secondary or tertiary amides 34. The primary alcohols 35 are prepared by reduction of the methyl esters 32 using lithium aluminum hydride.

The derivatives of formula I ($R^1$ is $-NR^6R^7$) were prepared according to the Schemes 8 and 9.

The aniline derivatives 38 were obtained in 3 steps from the triflates 15. Palladium catalyzed condensation of benzophenone imine with the triflates 15 afforded the imines 36 which were converted to the aniline derivatives 37 by treatment with ammonium hydroxide. Acidic or basic hydrolysis of 37 afforded the desired target compounds 38. The aniline derivatives 41 could also be obtained in 3 steps from the carboxylic acids 33 (Scheme 9). Curtius rearrangement of 33 afforded the Boc-protected anilines 39 which were deprotected under acidic conditions to give the anilines 40 (isolated as their dihydrochloride salts). Acylation of 40 with various acyl chloride in the presence of triethylamine provided the amides 41.

EXAMPLES

Materials: all chemicals were reagent grade and used without further purification. Analytical thin-layer chromatography (TLC) was performed on silica gel glass plates (250 microns) from Analtech and visualized by UV irradiation and iodine. Flash chromatography was conducted with silica gel (200-400 mesh, 60 Å, Aldrich). Chromatographic elution solvent systems are reported as volume:volume ratios. LC-MS data were obtained using a LC Thermo Finnigan Surveyor-MS Thermo Finnigan AQA in either positive mode or negative mode. Solvent A: 10 mM ammonium acetate, pH 4.5; solvent B: acetonitrile; solvent C: methanol; solvent D: water; column Waters Xterra C18 MS 2.0×50 mm, detector: PDA λ is 220-300 nM. Gradient program (positive mode): t=0.00, 600 µL/min, 99% A-1% B; t=0.30, 600 µL/min, 99% A-1% B; t=5.00, 600 µL/min, 1% A-99% B; t=5.30, 600 µL/min, 1% A-99% B. Gradient program (negative mode): t=0.00, 600 µL/min, 9% A-1% B-90% D; t=0.30, 600 µL/min, 9% A-1% B-90% D; t=5.00, 600 µL/min, 99% B-1% D; t=5.30, 600 µL/min, 99% B-1% D.

Preparation of Key Intermediate 7 (Scheme 1)

4(R)-(3-hydroxyphenyl)-3(R),4-dimethyl-1-tert-butyloxycarbonyl piperidine (2)

To a solution of (+) 4(R)-(3-hydroxyphenyl)-3(R),4-dimethyl-1-piperidine (1) (7 g, 0.034 mol, 1 eq) in anhydrous tetrahydrofuran (100 mL) was added portion wise tert-butyloxycarbonyl anhydride (8.2 g, 0.0375 mol, 1.1 eq). After the addition was complete, triethylamine (5.32 mL, 0.038 mol, 1.12 eq) was added and the mixture was stirred for 2 h at room temperature. The reaction mixture was poured into diethyl ether (300 mL) and washed consecutively with 1N aqueous HCl (100 mL), water (100 mL) and brine (100 mL). Drying over sodium sulfate followed by removal of the solvent under vacuum gave the crude titled product (10.5 g, 100%) used for the next step without further purification.

3(R),4-dimethyl-4(R)-(3-trifluoromethanesulfonyloxyphenyl)-1-tert-butyloxycarbonyl piperidine (3)

To a cold (0° C.) suspension of 2 (10.5 g, 0.034 mol, 1 eq) in anhydrous dichloromethane (100 mL), was added N-triphenyltrifluoromethane sulfonimide (13.51 g, 0.0378 mol, 1.1 eq) followed by addition of triethylamine (5.75 mL, 0.041 mol, 1.2 eq). The mixture was allowed to warm slowly to room temperature and stirring was continued for 2 h. The mixture was diluted with diethyl ether (200 mL) and washed successively with water (100 mL), aqueous 1N NaOH (3×100 mL), water (100 mL), and brine (100 mL). The organic layer was dried over sodium sulfate and concentrated under vacuum to furnish the crude product as a yellow oil. Purification by column chromatography (eluent: hexane/ethyl acetate=95:5) afforded the desired product (11.1 g, 74% 2 steps).

4(R)-(3-methoxycarbonylphenyl)-3(R),4-dimethyl-1-tertbutyloxycarbonyl piperidine (4)

To a stirred solution of 3 (10.8 g, 0.024 mol, 1 eq) in a mixture of methanol (100 mL) and dimethylsulfoxide (150 mL) was added triethylamine (7.55 mL, 0.054 mol, 2.2 eq). Carbon monoxide gas was bubbled through the mixture for 5 minutes. To the mixture was added palladium (II) acetate (0.554 g, 0.0024 mol, 0.1 eq) followed by 1,1'-bis(diphenylphosphino)ferrocene (2.73 g, 0.0049 mol, 0.2 eq). Carbon monoxide gas was bubbled through the mixture for 15 minutes and it was then stirred under an atmosphere of carbon monoxide and heated at 65° C. overnight. The mixture was cooled to room temperature and poured into water (500 mL). The mixture was extracted with ethyl acetate (3×150 mL). The combined organic extracts were washed with water (200 mL), brine (200 mL) and dried over sodium sulfate. Evaporation of the solvent under vacuum afforded a dark oil. The crude product was purified by column chromatography (eluent: hexane/ethyl acetate=95:5) affording the title compound (6.44 g, 75%).

4(R)-(3-methoxycarbonylphenyl)-3(R),4-dimethyl-1-piperidine hydrochloride (5)

An anhydrous solution of hydrochloric acid in diethyl ether (2M solution, 55 mL, 0.110 mol, 6 eq) was added to a solution of (4) (6.4 g, 0.018 mol, 1 eq) in anhydrous methanol (100 mL). The mixture was heated to reflux overnight, concentrated and dried under high vacuum. Trituration of the resulting mixture in diethyl ether (100 mL) afforded a white solid which was collected by filtration and washed with diethyl ether (3×20 mL) (5.11 g, 98%).

4(R)-(3-methoxycarbonylphenyl)-3(R),4-dimethyl-1-(2-trimethylsilylethyloxycarbonyl)piperidine (6)

To a suspension of 5 (1.31 g, 0.0046 mol, 1 eq) in anhydrous acetonitrile (15 mL) was added diisopropylethylamine (1.68 mL, 0.0096 mol, 2.1 eq) and 2-(trimethylsilyl)ethylpnitrophenylcarbonate (1.44 g, 0.0050 mol, 1.1 eq). The resulting solution was concentrated under vacuum and ethyl acetate (200 mL) was added. The organic layer was washed with aqueous 1N NaOH (100 mL), aqueous 1N HCl (100 mL), water (100 mL), brine (100 mL), dried over sodium sulfate and concentrated under vacuum. Purification of the crude product by column chromatography (eluent: hexane/ethyl acetate=95:5) afforded the title compound (1.67 g, 92%).

4(R)-(3-carboxyphenyl)-3(R),4-dimethyl-1-(2-trimethylsilylethyloxycarbonyl)piperidine (7)

A solution of lithium hydroxide monohydrate (2.75 g, 0.065 mol, 6 eq) in water (20 mL) was added drop wise to a cold (0° C.) solution of (6) (4.28 g, 0.0109 mol, 1 eq) in tetrahydrofuran (40 mL). The mixture was allowed to warm to room temperature and stirring was continued for 5 days. A 1N aqueous HCl solution (100 mL) was added to the mixture which was extracted with ethyl acetate (3×100 mL). The combined organic extracts were washed with water (100 mL), brine (100 mL) and dried over sodium sulfate. Evaporation of the solvent afforded the desired compound (4.0 g, 97%).

Preparation of Resin 8

To a suspension of the Wang resin (PL-Wang, 150-300 µM, 1.7 mmol/g, 1.6 g, 0.0027 mol, 1 eq) (Scheme 2) in a mixture dichloromethane/dimethylformamide 9:1 (30 mL) was added consecutively 4(R)-(3-carboxyphenyl)-3(R),4-dimethyl-1-(2-trimethylsilylethyloxycarbonyl)piperidine (7) (2.55 g, 0.0067 mol, 2.5 eq), 4-dimethylaminopyridine (DMAP) (0.370 g, 0.0030 mol, 1.12 eq) and diisopropylcarbodiimide (1.27 mL, 0.008 mol, 3 eq). The mixture was shaken for 7 h at room temperature. The resin was then drained, washed consecutively with dimethylformamide (5×), dimethylformamide/water (9:1) (5×), dimethylformamide (5×), methanol (5×), dichloromethane (5×), diethylether (5×) and dried under vacuum. Qualitative analysis of the resin was performed by single bead FT-IR ν (C=O) ester:1715 cm$^{-1}$; ν (C=O) carbamate:1696 cm$^{-1}$ Preparation of Resin 9

The resin 8 (estimated loading: 80%; 1.36 mmol/g, 2.67 g, 0.0036 mol) was swelled in anhydrous tetrahydrofuran (30 mL), treated with a 1M solution of tetrabutylammonium fluoride in tetrahydrofuran (18.15 mL, 0.018 mol, 5 eq) and shaken for 16 h at room temperature. The resin was drained, washed with THF (5×), treated with THF/water 1:1 (30 mL) and shaken at room temperature for 2 hours. The resin was drained and further washed consecutively with dimethylformamide (5×), dimethylformamide/water (9:1) (5×), dimethylformamide (5×), methanol (5×), dichloromethane (5×), diethylether (5×). Qualitative analysis of the TeoC deprotection was conducted using single bead FT-IR.

General Procedure for Reductive Amination on Solid Support

Preparation of Resin 11

A 1 N solution of aldehyde or ketone (130 µL, 0.00017 mol, 14 eq) in a mixture N-methylpyrrolidinone/ethanol 3:1 was added to the resin 9 (10 mg, estimated loading: 1.22 mmol/g, 0.0000122 mol, 1 eq) and the mixture was shaken overnight at room temperature (imine formation). A 8 N solution of borane in pyridine (210 µL, 0.00017 mol, 14 eq) was then added to the mixture which was shaken for 4 days at room temperature. The resin was then drained, washed consecutively with dimethylformamide (5×), dimethylformamide/water (9:1) (5×), dimethylformamide (5×), methanol (5×), dichloromethane (5×), diethylether (5×), and dried under vacuum. For Example 1, cyclohexanone was used as the ketone reagent.

General Procedure for Cleavage of Resin 11

The resin 11 (10 mg) was shaken in a mixture trifluoroactic acid/dichloromethane (1:1) (300 µL) at room temperature for 20 min. the filtrate was collected and the resin was further washed with dichloromethane (300 µL) and acetonitrile (300 µL). Evaporation of the filtrate afforded the desired compound.

Example 1

Preparation of 3-(1-Cyclohexyl-3R,4R-dimethyl-piperidin-4-yl)-benzoic acid (12)

The title compound 12 was synthesized using the general experimental protocol outlined previously using cyclohexanone as the ketone reagent. For Example 1, $R_4$ is cyclohexyl; Mass spectral analysis: m/z=316 (M+H)$^+$

Example 2

Preparation of (3-(3R,4R-Dimethyl-piperidin-4-yl)-benzoic acid (10)

The resin 9 (10 mg) was shaken in a mixture trifluoroacetic acid/dichloromethane (1:1) (300 µL) at room temperature for 20 minutes. The filtrate was collected and the resin was further washed with dichloromethane (300 µL) and acetonitrile (300 µL). Evaporation of the filtrate afforded the desired title compound; For Example 2, $R_4$ is H; Mass spectral analysis: m/z=234 (M+H)$^+$ Using procedures described above for Example 1, Examples 3-26 were prepared (Table 1).

Example 27

3-[1-(2S-Carboxy-3-phenyl-propyl)-3R,4R-dimethyl-piperidin-4-yl]-benzoic acid (17a)

To a cold (0° C.) solution of methyl (αR,3R,4S)-4-(3-hydroxyphenyl)-3,4-dimethyl-α-(phenylmethyl)-1-piperidinepropanoate hydrochloride (14a) (1.5 g, 0.003 mmol, 1 eq) in anhydrous dichloromethane (15 mL) was added triethylamine (1.2 mL, 0.0086 mmol, 2.4 eq) followed by N-triphenyltrifluoromethane sulfonimide (1.41 g, 0.0039 mmol, 1.1 eq). The mixture was allowed to warm slowly to room temperature and stirring was continued for 2 h. The mixture was diluted with diethyl ether (200 mL) and washed successively with water (100 mL), aqueous 1N NaOH (3×100 mL), water (100 mL), and brine (100 mL). The organic layer was dried over sodium sulfate and concentrated under vacuum to furnish the crude product as a yellow oil. Purification by column chromatography (eluent: hexane/ethyl acetate=95:5) afforded the desired product 15a (1.72 g, 93%); Mass spectral analysis: m/z=514 (M+H)$^+$.

To a stirred solution of 15a (1.72 g, 0.0033 mol, 1 eq) in a mixture of methanol (15 mL) and dimethylsulfoxide (20 mL) was added triethylamine (1.03 mL, 0.0073 mol, 2.2 eq). Carbon monoxide gas was bubbled through the mixture for 5 minutes. To the mixture was added palladium (II) acetate (0.075 g, 0.00033 mol, 0.1 eq) followed by 1,1'-bis(diphenylphosphino)ferrocene (0.371 g, 0.00067 mol, 0.2 eq). Carbon monoxide gas was bubbled through the mixture for 15 minutes and it was then stirred under an atmosphere of carbon monoxide and heated at 65° C. overnight. The mixture was cooled to room temperature and poured into water (100 mL). The mixture was extracted with ethyl acetate (3×50 mL). The combined organic extracts were washed with water (100 mL), brine (100 mL) and dried over sodium sulfate. Evaporation of the solvent under vacuum afforded an oil. The crude product was purified by column chromatography (eluent: hexane/ethyl acetate=95:5) affording the desired compound 16a (0.720 g, 51%); Mass spectral analysis: m/z=424 (M+H)$^+$.

A solution of aqueous 2N sodium hydroxide (2.55 mL, 0.00509 mol, 6 eq) was added drop wise to a cold (0° C.) solution of 16a (0.360 g, 0.00084 mol, 1 eq) in tetrahydrofuran (10 mL). The mixture was allowed to warm to room temperature and stirring was continued for 5 hours. A solution of lithium hydroxide monohydrate (0.213 g, 0.0050 mol, 6 eq) in water (5 mL) was added to the mixture [methanol (3 mL) was added for solubilization] and stirring was continued for 12 hours. A 12N aqueous HCl solution (0.8 mL) was added to neutralize the mixture which was concentrated under vacuum. The precipitate was collected by filtration and washed with diethylether. The desired compound 17a (Example 27) was obtained as a white solid (0.2 g, 64%); Mass spectral analysis: m/z=396 (M+H)$^+$

Example 28

Preparation of [[2(R)-[[4(R)-(3-carboxyphenyl)-3(R),4-dimethyl-1-piperidinyl]methyl]-1-oxo-3-phenylpropyl]amino]acetic Acid (17b)

To a suspension of (αR,3R,4S)-4-(3-hydroxyphenyl)-3,4-dimethyl-α-(phenylmethyl)-1-piperidinepropanoic acid (13) (4 g, 0.88 mmol), glycine tert-butyl ester hydrochloride (2 g, 11.96 mmol, 1.1 eq) and hydroxybenzotriazole (1.62 g, 11.96 mmol, 1.1 eq) in anhydrous tetrahydrofuran (35 mL) was added under nitrogen triethylamine (1.67 mL, 11.96 mmol, 1.1 eq) followed by a solution of dicyclohexylcarbodiimide (2.47 g, 11.96 mmol, 1.1 eq) in anhydrous tetrahydrofuran (15 mL) (Scheme 3). The reaction mixture was stirred at room temperature for 60 h, cooled to 0° C. for 30 minutes and filtered. The filtrate was concentrated under vacuum and ethyl acetate (100 mL) was added. The solution was washed with and saturated aqueous solution of sodium carbonate (100 mL) and brine (100 mL). The organic layer was dried over sodium sulfate, filtered and placed in a fridge overnight to allow residual traces of dicyclohexylurea to precipitate. The suspension was then filtered and the filtrate was concentrated to give compound 14b as yellow foam (6 g, 100%). Mass spectral analysis: m/z=481 (M+H)$^+$ To a solution of 14b (0.1 g, 0.208 mmol, 1 eq) in anhydrous dichloromethane (1 mL) was added triethylamine (48 µL, 0.345 mmol, 1.66 eq) followed by drop wise addition of a solution of N-triphenyltrifluoromethane sulfonimide (0.111 g, 0.312 mmol, 1.5 eq) in anhydrous dichloromethane (0.1 mL) at room temperature under argon. The reaction mixture was allowed to stir at room temperature overnight. The reaction mixture was washed with aqueous 1N NaOH solution (2 mL) and concentrated under vacuum. The residue was then resuspended in dichloromethane (5 mL) and aqueous 1N NaOH solution (2 mL) and stirred at room temperature for 30 minutes. The organic layer was separated and the aqueous phase was extracted with dichloromethane (3×2.5 mL). The combined organic extracts were washed with aqueous 1N NaOH solution (2 mL) and dried over sodium sulfate. The mixture was filtered and the filtrate was concentrated to afford 15b as a red colored clear oil. (0.133 g, 100%). Mass spectral analysis: m/z=613 (M+H)$^+$ A solution of (15b) (0.5 g, 0.816 mmol, 1 eq), palladium acetate (36.2 mg, 20 mol %, 0.163 mmol), diphenylphoshinopropane (65.2 mg, 20 mol %, 0.163 mmol), triethylamine (284 µL, 2.026 mmol, 2.5 eq) in anhydrous dimethylformamide (10 mL) and methanol (6 mL) was purged with CO(g) for 10 minutes and the reaction mixture was stirred for 16 hours at 70° C. under a carbon monoxide atmosphere (Scheme 3). The mixture was concentrated under vacuum and purified by column chromatography (eluent: dichloromethane/methanol=98:2). (0.421 g, 99%). For 16b mass spectral analysis: m/z=523 (M+H)$^+$ To a solution of 16b (0.350 g, 0.670 mmol, 1 eq) in tetrahydrofuran (50 mL) was added an aqueous 1N NaOH solution (50 mL) and the reaction mixture was stirred at room temperature for 16 h. The reaction mixture was concentrated and the pH was adjusted to 4. The mixture was extracted with chloroform/isopropanol (3:1, 150 mL). The organic extract was dried over sodium sulfate and concentrated to afford the title compound 17b (Example 28) (0.142 g, 50%). Mass spectral analysis: m/z=453 (M+H)+

Example 29

Preparation of 3-(1-{2-[3-(4-Hydroxyphenyl)-propionylamino]-3-methyl-butyl}-3R,4R-dimethyl-piperidin-4-yl)benzoic acid (21)

To a solution of Dess-Martin periodinane (3.12 g, 0.0073 mol, 1.5 eq) in dichloromethane (25 mL) was added a solution of N-Boc-L-valinol (1 g, 0.0049 mol, 1 eq) in dichloromethane (25 mL). The reaction mixture was stirred at room temperature for 3 h and was diluted with diethyl ether (50 mL). The mixture was poured into an aqueous saturated solution of sodium bicarbonate (100 mL) containing sodium thiosulfate (8.16 g, 10.5 eq). The mixture was stirred for 30 min and the layers were separated. The ether layer was washed with an aqueous saturated solution of sodium bicarbonate (50 mL), water (50 mL), dried (sodium sulfate) and filtered. The filtrate was concentrated to give the crude (1-formyl-2-methyl-propyl)-carbamic acid tert-butyl ester used for the next step without further purification.

An 8 M solution of borane in pyridine (1.43 mL, 0.0114 mol, 2.75 eq) was added to a solution of (1-formyl-2-methyl-propyl)-carbamic acid tert-butyl ester (N-Boc-L-valinal) (2.3 g, 0.01142 mol, 2.75 eq), 4(R)-(3-methoxycarbonylphenyl)-3(R),4-dimethyl-1-piperidine hydrochloride (5) (1.18 g, 0.00415 mol, 1 eq) and triethylamine (0.64 mL, 0.0045 mol, 1.1 eq) in methanol (15 mL). The mixture was stirred for 6 h at room temperature and concentrated under vacuum. Purification of the crude product by column chromatography (eluent: dichloromethane/methanol=98:2) afforded the desired compound 18 (0.280 g, 15%); Mass spectral analysis: m/z=433 (M+H)+

An anhydrous solution of hydrochloric acid in diethyl ether (2M solution, 1.94 mL, 0.0038 mol, 6 eq) was added to a solution of 18 (0.280 g, 0.00064 mol, 1 eq) in anhydrous methanol (20 mL). The mixture was heated to reflux overnight, concentrated and dried under high vacuum. Trituration of the resulting mixture in diethyl ether (10 mL) afforded a white solid (19) which was collected by filtration and washed with diethyl ether (0.250 g, 95%); Mass spectral analysis: m/z=333 (M+H)+

To a suspension of 19 (0.420 g, 0.0010 mol, 1 eq), BOP reagent (0.458 g, 0.0010 mol, 1 eq) and triethylamine (0.75 mL, 0.0054 mol, 5.2 eq) in tetrahydrofuram (30 mL) was added 3-(4-hydroxyphenyl)propionic acid (0.206 g, 0.0012 mol, 1.2 eq) and the mixture was stirred for 3 hours at room temperature. Diethyl ether (100 mL) was added and the solution was poured into an aqueous saturated solution of sodium bicarbonate (50 mL). The organic layer was separated, washed with water, dried (sodium sulfate), filtered and concentrated.

The crude product was purified by column chromatography (eluent: dichloromethane/methanol=95:5) affording the desired compound 20 (0.300 g, 60%); Mass spectral analysis: m/z=481 (M+H)+

A solution of lithium hydroxide monohydrate (0.078 g, 0.0018 mol, 6 eq) in water (1 mL) was added to a cold (0° C.) solution of 20 (0.150 g, 0.00031 mol, 1 eq) in tetrahydrofuran (10 mL). Methanol (3 mL) was added for solubilization. The mixture was allowed to warm to room temperature and stirring was continued for 12 hours. A 12N aqueous HCl solution was added to neutralize the mixture which was concentrated under vacuum. The precipitate was collected by filtration and washed with diethylether. The desired compound 21 (Example 29) was obtained as a white solid (0.090 g, 62%); Mass spectral analysis: m/z=467 (M+H)+

Preparation of Resin 23

A solution dimethylformamide/piperidine 75:25 (3 mL) was added to the rink amide resin (1.06 mmol/g, 0.185 g, 0.00057 mol, 1 eq) and the suspension was mixed at room temperature for 1 hour (Scheme 5). The resin was then drained, washed consecutively with dimethylformamide (5×), dimethylformamide/water (9:1) (5×), dimethylformamide (5×), methanol (5×), dichloromethane (5×), diethylether (5×) and dried under vacuum. To a suspension of the resulting resin in a mixture dichloromethane/dimethylformamide 9:1 (5 mL) was added consecutively diisopropylethylamine (0.24 mL, 0.00143 mol, 2.5 eq), 4(R)-(3-carboxyphenyl)-3(R),4-dimethyl-1-(2-trimethylsilylethyloxycarbonyl) piperidine (7) (0.54 g, 0.00143 mol, 2.5 eq), 1-hydroxybenzotriazole (0.015 g, 0.0001 mol, 0.2 eq) and HATU (0.545 g, 0.00143 mol, 2.5 eq). The mixture was shaken overnight at room temperature. The resin was then drained, washed consecutively with dimethylformamide (5×), dimethylformamide/water (9:1) (5×), dimethylformamide (5×), methanol (5×), dichloromethane (5×), diethyl-ether (5×) and dried under vacuum.

Preparation of Resin 24

The resin 23 (estimated loading: 100%; 1.06 mmol/g, 4 g, 4.24 mmol) was swelled in anhydrous tetrahydrofuran (30 mL), treated with a 1 M solution of tetrabutylammonium fluoride in tetrahydrofuran (21.2 mL, 21.2 mmol, 5 eq) and shaken for 16 hours at room temperature. The resin was drained, washed with THF (5×), then treated with THF/water 1:1 (60 mL) and shaken at room temperature for 2 hours. The resin was drained and further washed consecutively with dimethylformamide (5×), dimethylformamide/water (9:1) (5×), dimethylformamide (5×), methanol (5×), dichloromethane (5×), diethylether (5×). General procedure for reductive amination on solid support Preparation of Resin 26

A 5 N solution of aldehyde or ketone (0.16 mL, 0.000848 mol, 10 eq) in N-methylpyrrolidinone was added to a suspension of the resin 24 (80 mg, estimated loading: 1.06 mmol/g, 0.0000848 mol, 1 eq) in a mixture N-methylpyrrolidinone/ethanol 3:1 (2 mL) and the mixture was shaken for 1 h at room temperature (imine formation). A 8N solution of borane in pyridine (0.10 mL, 0.000848 mol, 10 eq) was then added to the mixture which was shaken for 4 days at room temperature. The resin was then drained, washed consecutively with dimethylformamide (5×), dimethylformamide/water (9:1) (5×), dimethylformamide (5×), methanol (5×), dichloromethane (5×), diethylether (5×), and dried under vacuum. For Example 30, cyclohexanone was used as the ketone reagent.

General Procedure for Cleavage of Resin 26

The resin 26 (30 mg) was shaken in a mixture trifluoroacetic acid/dichloromethane (1:1) (300 µL) at room temperature for 20 minutes. The filtrate was collected and the resin was further washed with dichloromethane (300 µL) and acetonitrile (300 µL). Evaporation of the filtrate afforded the desired compound.

Example 30

Preparation of 3-(1-Cyclohexyl-3R,4R-dimethyl-piperidin-4-yl)-benzamide (27)

The title compound 27 was synthesized using the general experimental protocol for reductive amination on a solid support outlined previously using cyclohexanone as the ketone reagent. Example 30: $R_4$ is cyclohexyl; Mass spectral analysis: m/z=315 $(M+H)^+$

Example 31

Preparation of 3-(3R,4R-Dimethyl-piperidin-4-yl)-benzamide (25)

The resin 24 (10 mg) was shaken in a mixture trifluoroactic acid/dichloromethane (1:1) (300 µL) at room temperature for 20 minutes. The filtrate was collected and the resin was further washed with dichloromethane (300 µL) and acetonitrile (300 µL). Evaporation of the filtrate afforded the desired title compound. For Example 31, $R_4$ is H; Mass spectral analysis: m/z=233 $(M+H)^+$ Using procedures described above for Example 30, Examples 32-57 were prepared (Table 2).

Example 58

Preparation of [[2(R)-[[4(R)-(3-amidophenyl)-3(R),4-dimethyl-1-piperidinyl]methyl]-1-oxo-3-phenyl-propyl]amino]acetic Acid (29b)

A stirred solution of 15b (0.5 g, 0.816 mmol, 1 eq), palladium chloride (9 mg, 6 mol %, 48.96 µmol), diphenylphosphinopropane (39 mg, 12 mol %, 97.9 µmol) and $HN(TMS)_2$ (0.69 mL, 3.264 mmol, 4 eq) was purged with CO(g) for 5 minutes, then stirred under an atmosphere of CO(g) for 1 hour at 80° C. After this time was added palladium acetate (18 mg, 10 mol %, 0.0816 mmol) and diphenylphosphinopropane (65 mg, 0.163 mmol). This mixture was purged with CO(g) for 10 minutes, then stirred under an atmosphere of CO(g) for 4 hours at 85-90° C. The reaction mixture was concentrated under vacuum and partitioned between dichloromethane (50 mL) and water (50 mL). The aqueous layer was extracted with dichloromethane (2×50 mL). The combined organic extracts were washed with brine (50 mL), dried over sodium sulfate and concentrated. The crude product was purified by column chromatography (eluent: dichloromethane/methanol=97.5:2.5) affording compound 28b as a yellow foamy solid. (0.170 g, 41%); Mass spectral analysis: m/z=508 $(M+H)^+$ A solution of 28b (0.170 g, 0.335 mmol, 1 eq) in 4N HCl in dioxane (7.5 mL) was stirred at room temperature for 2.5 hours. The solvent was removed under vacuum affording a yellow crystalline solid. The crude product was purified by preparative HPLC (methanol/water/TFA) affording the title compound 29b (Example 58) as the TFA salt (0.098 g, 55%); Mass spectral analysis: m/z=452 $(M+H)^+$

Example 59

Preparation of 3-(1-{2-[3-(4-Hydroxyphenyl)-propionylamino]-3-methyl-butyl}-3R,4R-dimethyl-piperidin-4-yl)benzamide (22)

To a suspension of the acid 21 (0.190 g, 0.00040 mol, 1 eq) and triethylamine (0.18 mL, 0.0013 mol, 3.2 eq) in dimethylformamide (10 mL) was added ammonium chloride (0.109 g, 0.0020 mol, 5 eq), hydroxybenzotriazole (0.066 g, 0.00048 mol, 1.2 eq) and EDCI (0.109 g, 0.00057 mol, 1.4 eq) and the mixture was stirred for 24 hours at room temperature. The mixture was poured into an aqueous saturated solution of sodium bicarbonate (50 mL) and extracted with ethyl acetate. The organic layer was separated, washed with water, dried (sodium sulfate), filtered and concentrated. The crude product was purified by column chromatography (eluent: dichloromethane/methanol=95:5) affording the desired compound 22 (Example 59) (0.110 g, 58%); Mass spectral analysis: m/z=466 $(M+H)^+$

Example 60

Preparation of [[2(R)-[[4(R)-(3-aminophenyl)-3(R),4-dimethyl-1-piperidinyl]methyl]-1-oxo-3-phenyl-propyl]amino]acetic Acid (38b)

A mixture of 15b (0.250 g, 0.408 mmol, 1 eq), diphenylphosphinopropane (34 mg, 15 mol %, 61.20 µmol), $Pd_2(dba)_3$ (18.7 mg, 5 mol %, 20.4 µmol), sodium tert-butoxide (86.3 mg, 0.898 mmol, 2.2 eq), benzophenoneimine (82.2 µL, 0.489 mmol, 1.2 eq) in anhydrous toluene was degassed using argon and was then heated to 80° C. for 17 hours. The reaction mixture was cooled to room temperature and quenched by addition of an aqueous saturated solution of ammonium chloride (25 mL). The organic layer was separated and the aqueous layer was further extracted with dichloromethane (2×25 mL). The combined organic extracts were washed with brine (25 mL), dried over sodium sulfate and concentrated. Purification of the crude product by column chromatography (eluent: dichloromethane/methanol=1:1) afforded the compound 36b as a tan solid (0.136 g, 52%).

A mixture of 36b (0.136 g, 0.211 mmol, 1 eq), hydroxylamine hydrochloride (30 mg, 0.425 mmol, 2 eq), sodium acetate (87 mg, 1.056 mmol, 5 eq) and methanol (2.5 mL) was stirred at room temperature for 45 minutes under argon. The solvent was removed in vacuo and the reaction mixture was extracted with dichloromethane (20 mL). The aqueous layer was further extracted with dichloromethane (2×20 mL). The combined organic extracts were washed with an aqueous saturated solution of sodium bicarbonate (20 mL), dried over sodium sulfate and concentrated. Purification of the crude product by column chromatography (eluent: dichloromethane/methanol=97.5:2.5) afforded the desired product 37b (62 mg, 61%); Mass spectral analysis: m/z=480 $(M+H)^+$ A solution of 37b (0.170 g, 0.335 mmol, 1 eq) in 4N HCl in dioxane (7.5 mL) was stirred at room temperature for 1 h 30 min. The solvent was removed under vacuum. The crude product was purified by preparative HPLC (acetonitrile/water/TFA) affording the title compound 38b (Example 60) as the diTFA salt (0.100 g, 74%); Mass spectral analysis: m/z=424 $(M+H)+$ Scheme 1

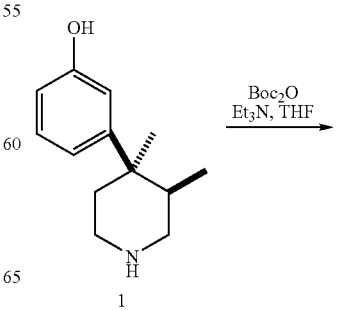

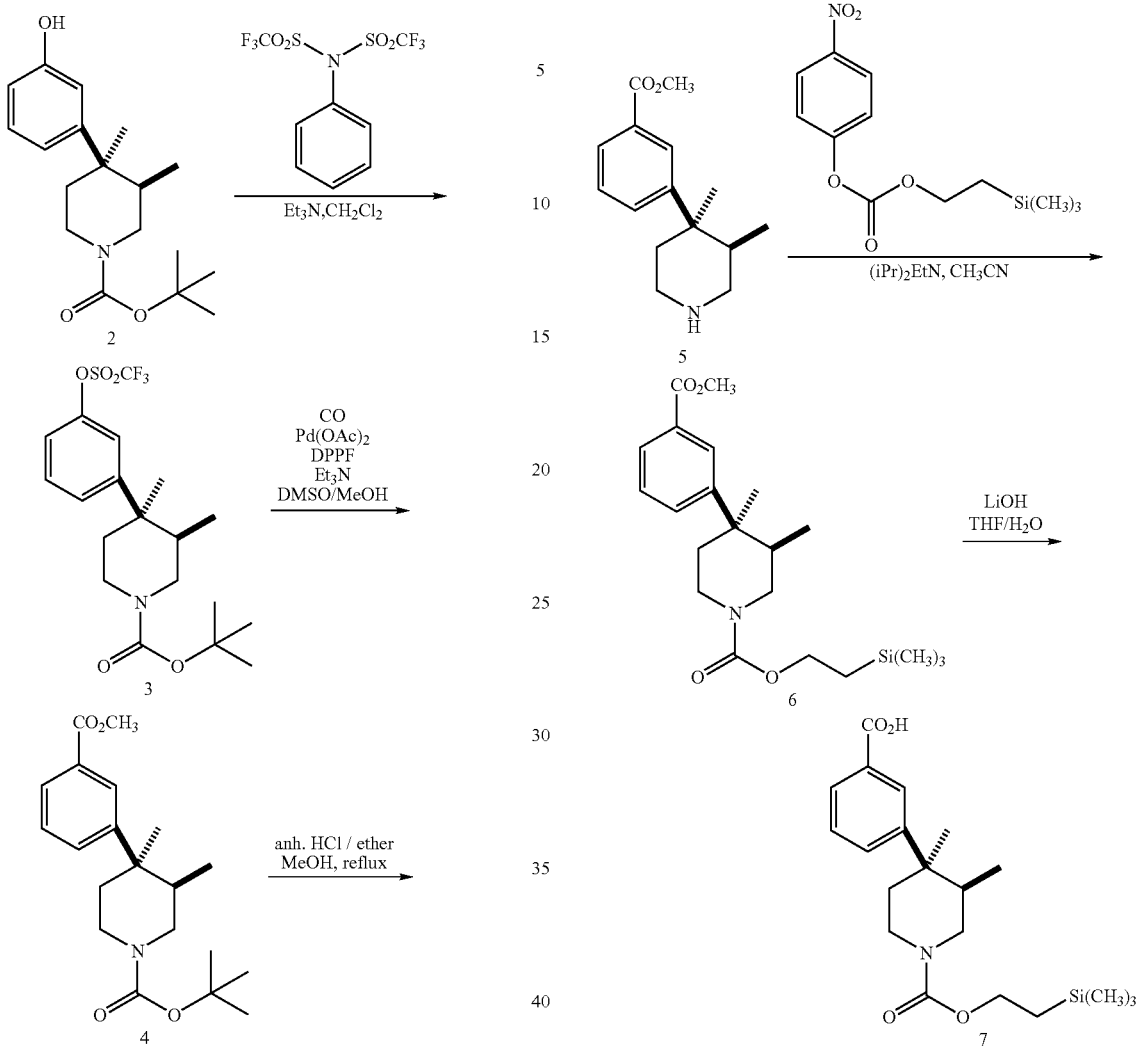
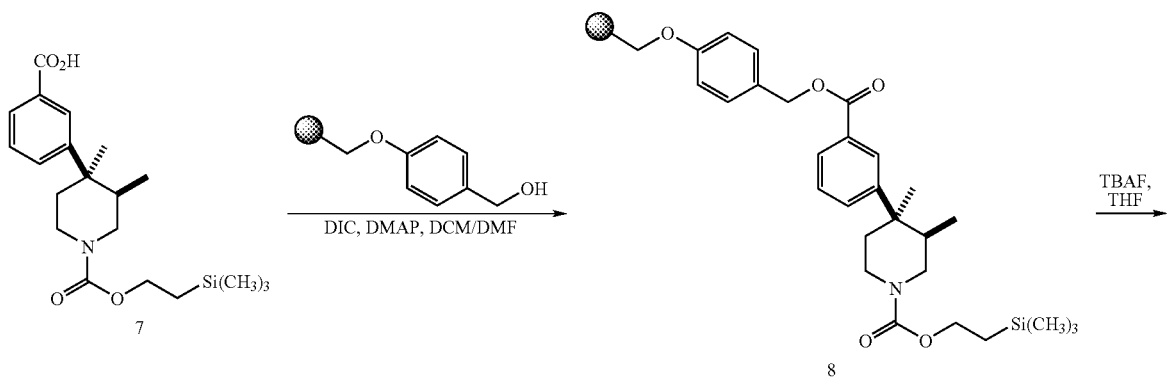
Scheme 2

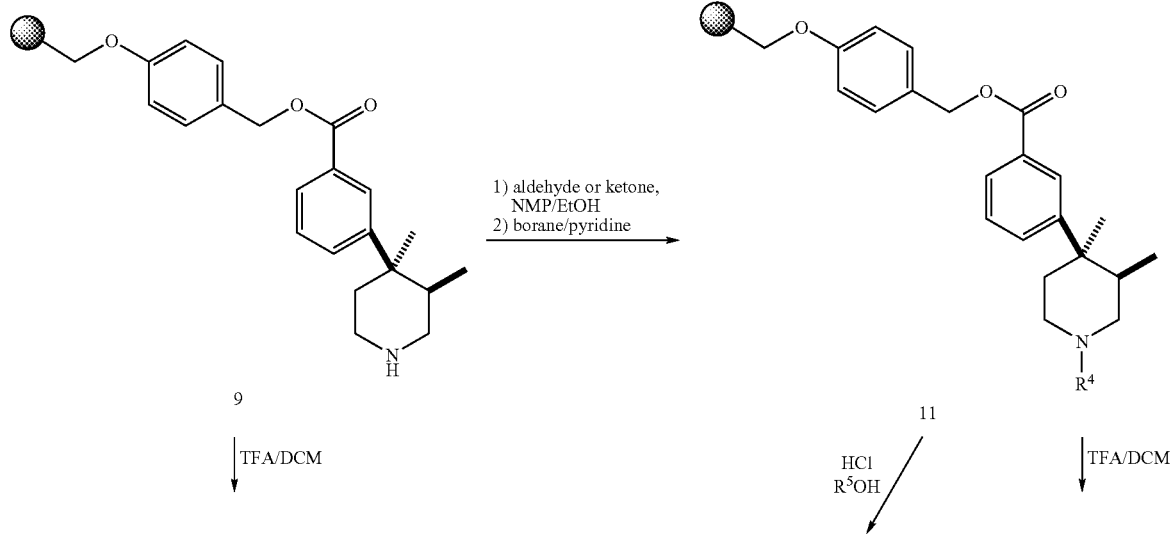
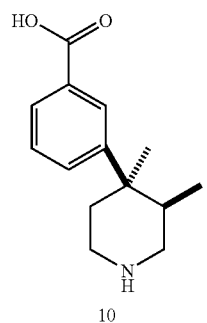
10
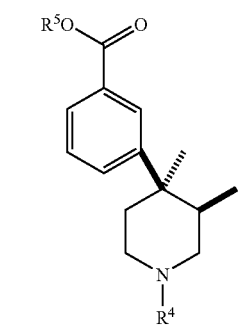
Formula I
(R⁵ = alkyl, arylalkyl, heteroalkyl)
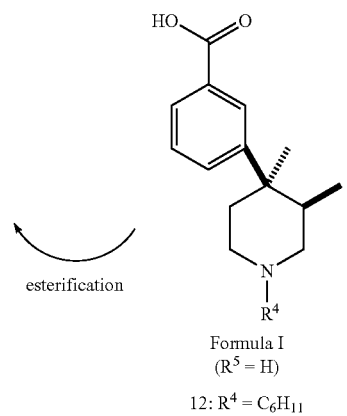
Formula I
(R⁵ = H)
12: R⁴ = C₆H₁₁
Scheme 3
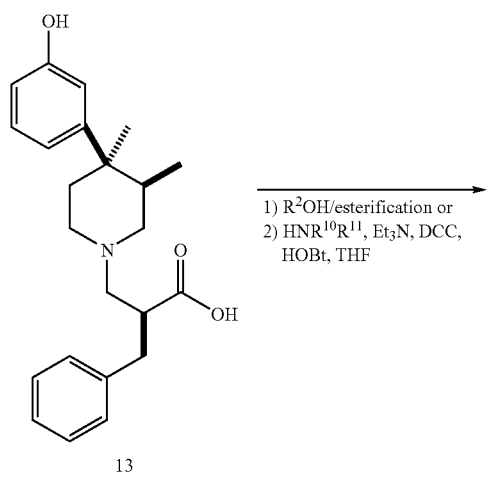
13
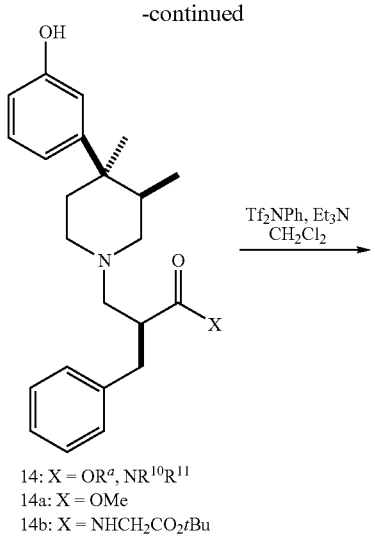
14: X = OR^a, NR¹⁰R¹¹
14a: X = OMe
14b: X = NHCH₂CO₂tBu -continued
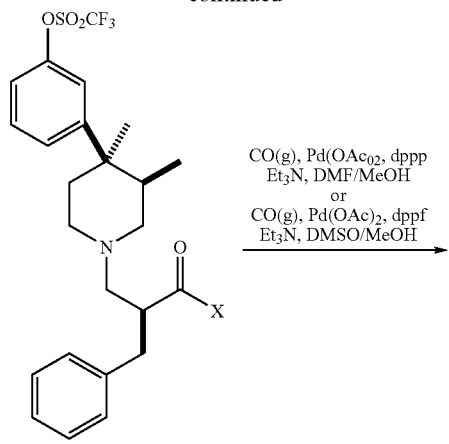
15: X = OR$^a$, NR$^{10}$R$^{11}$
15a: X = OMe
15b: X = NHCH$_2$CO$_2$tBu
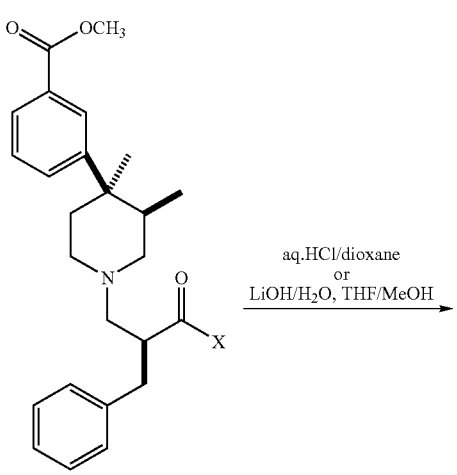
16: X = OR$^a$, NR$^{10}$R$^{11}$
16a: X = OMe
16b: X = NHCH$_2$CO$_2$tBu
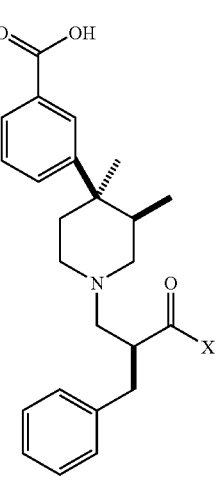
17: X = OR$^a$, NR$^{10}$R$^{11}$
17a: X = OH
17b: X = NHCH$_2$CO$_2$H
Scheme 4
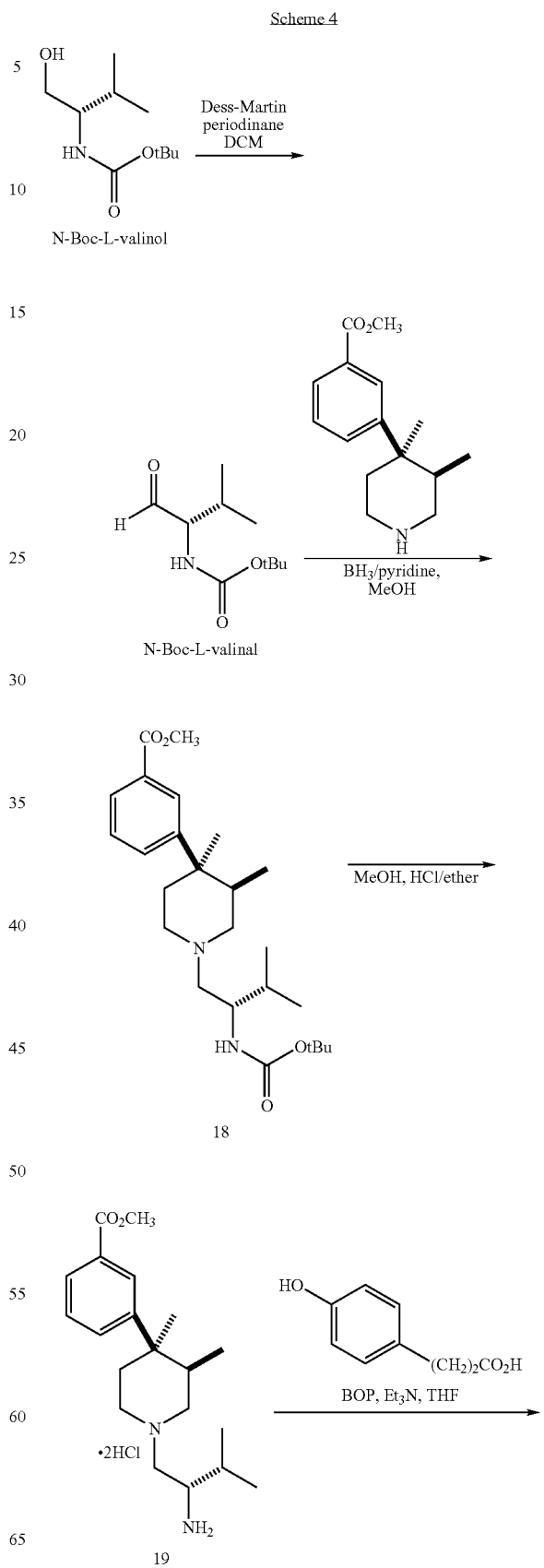
18
19

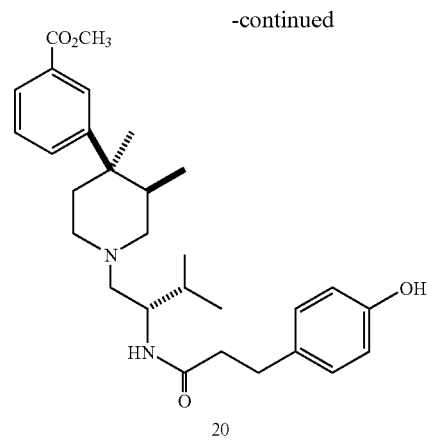
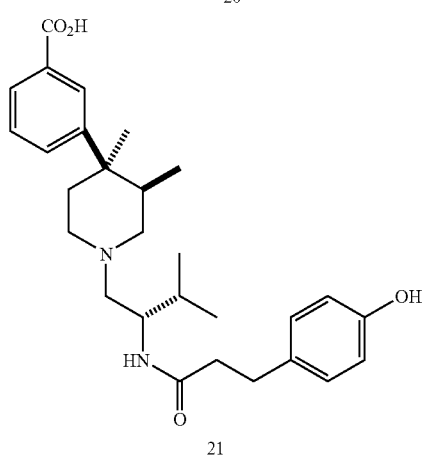
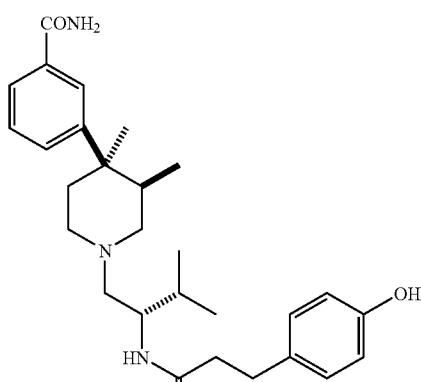
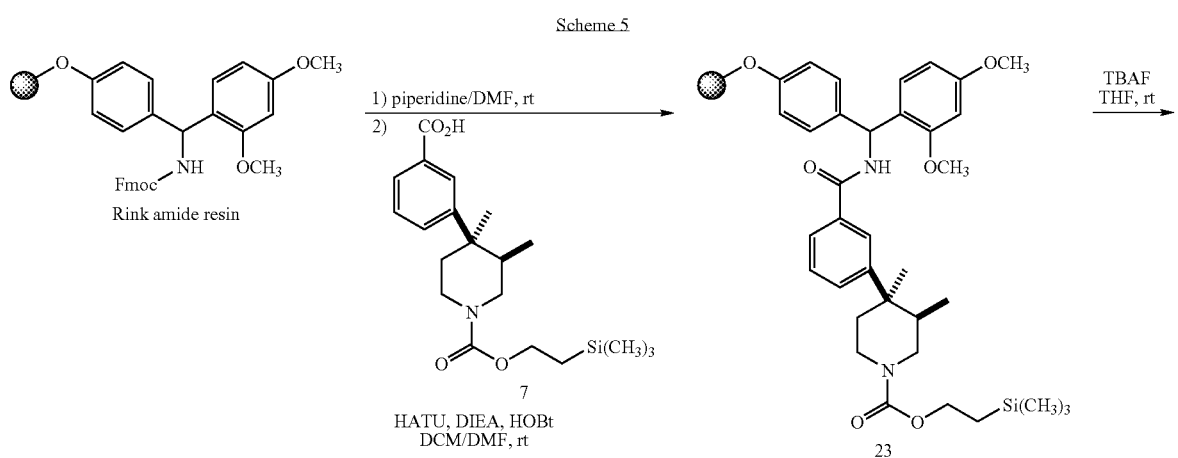

-continued
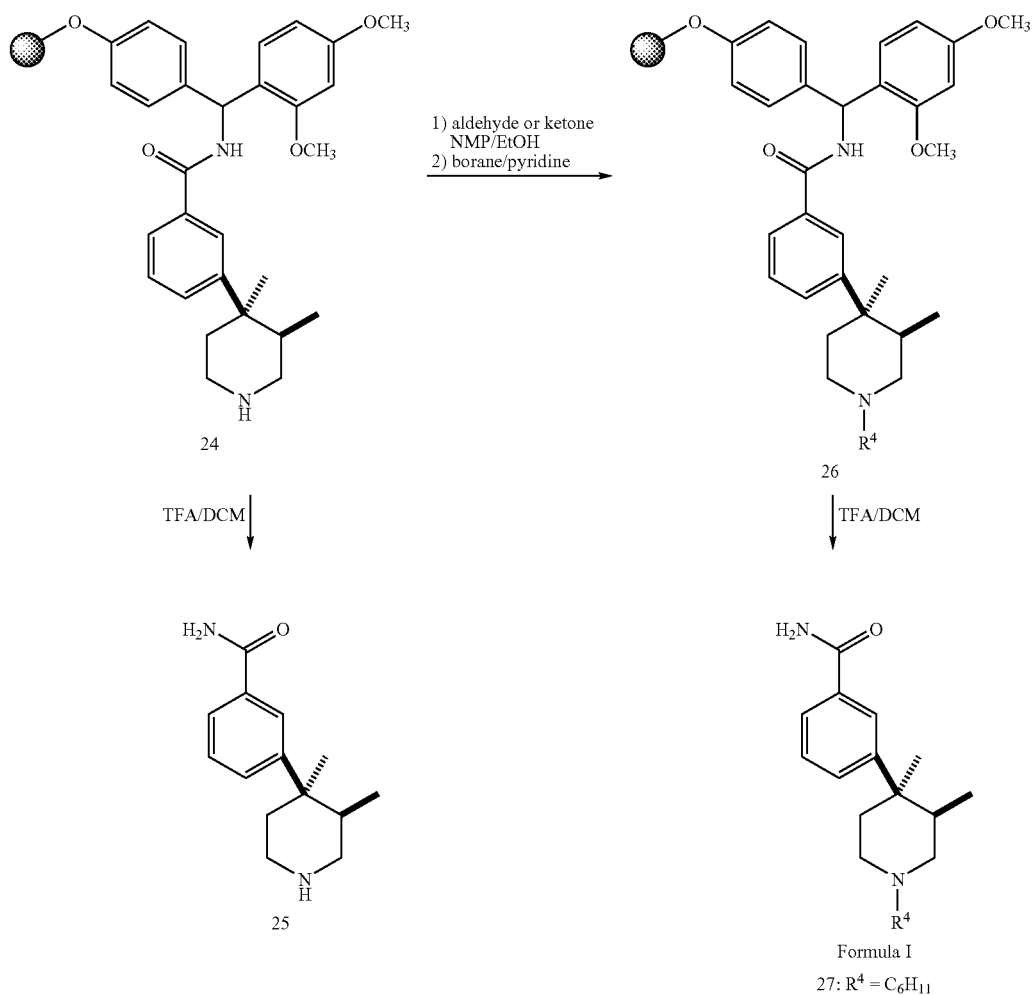
Formula I
27: R⁴ = C₆H₁₁
Scheme 6
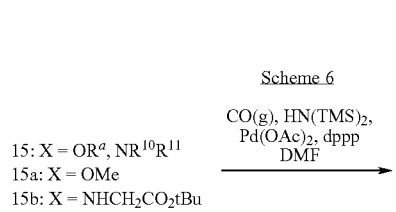
15: X = OR$^a$, NR$^{10}$R$^{11}$
15a: X = OMe
15b: X = NHCH₂CO₂tBu
CO(g), HN(TMS)₂,
Pd(OAc)₂, dppp
DMF
→
-continued
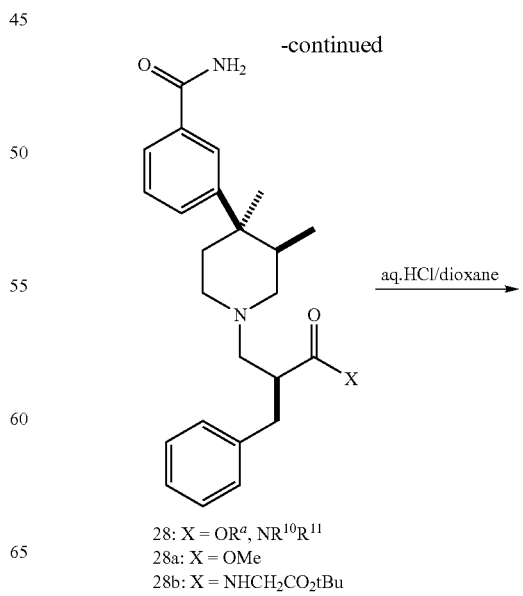
aq.HCl/dioxane
→
28: X = OR$^a$, NR$^{10}$R$^{11}$
28a: X = OMe
28b: X = NHCH₂CO₂tBu

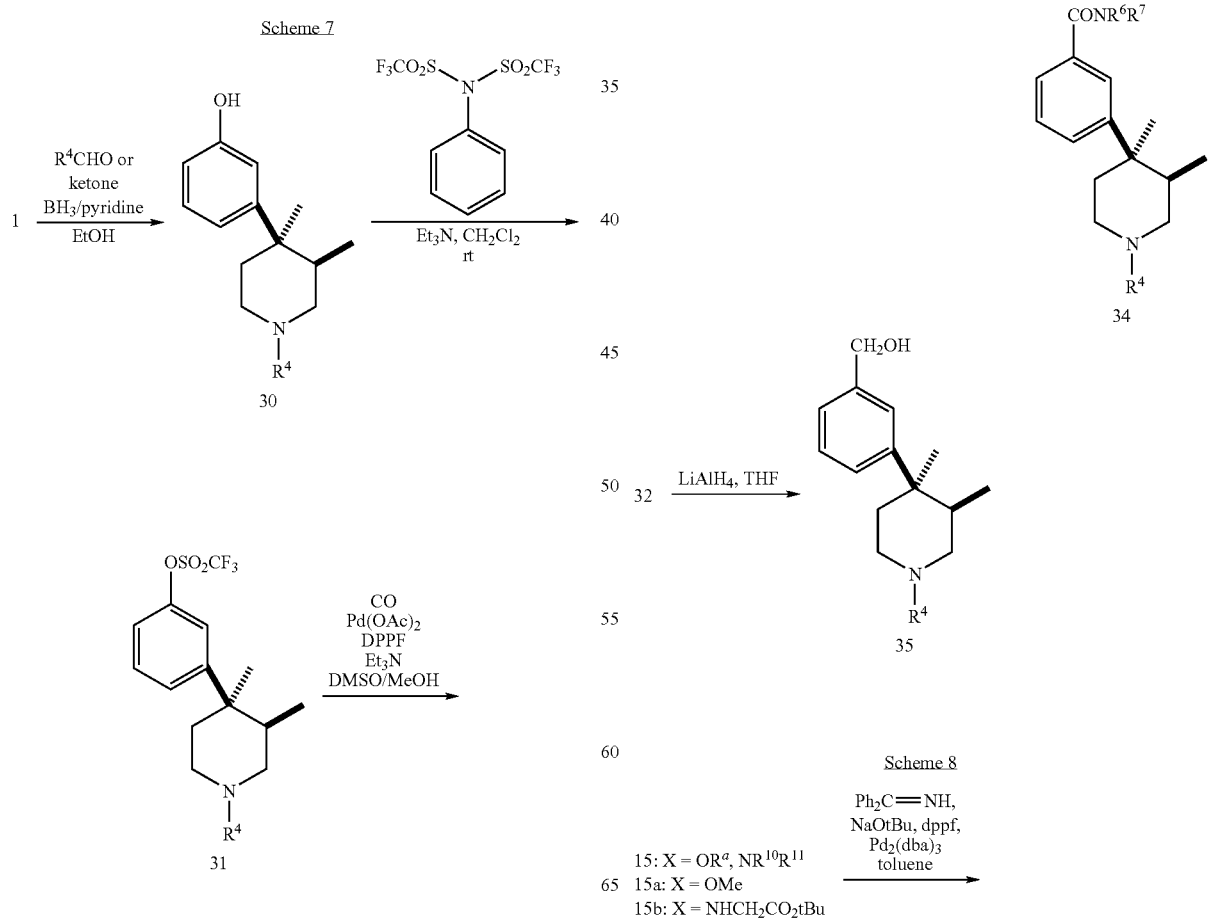

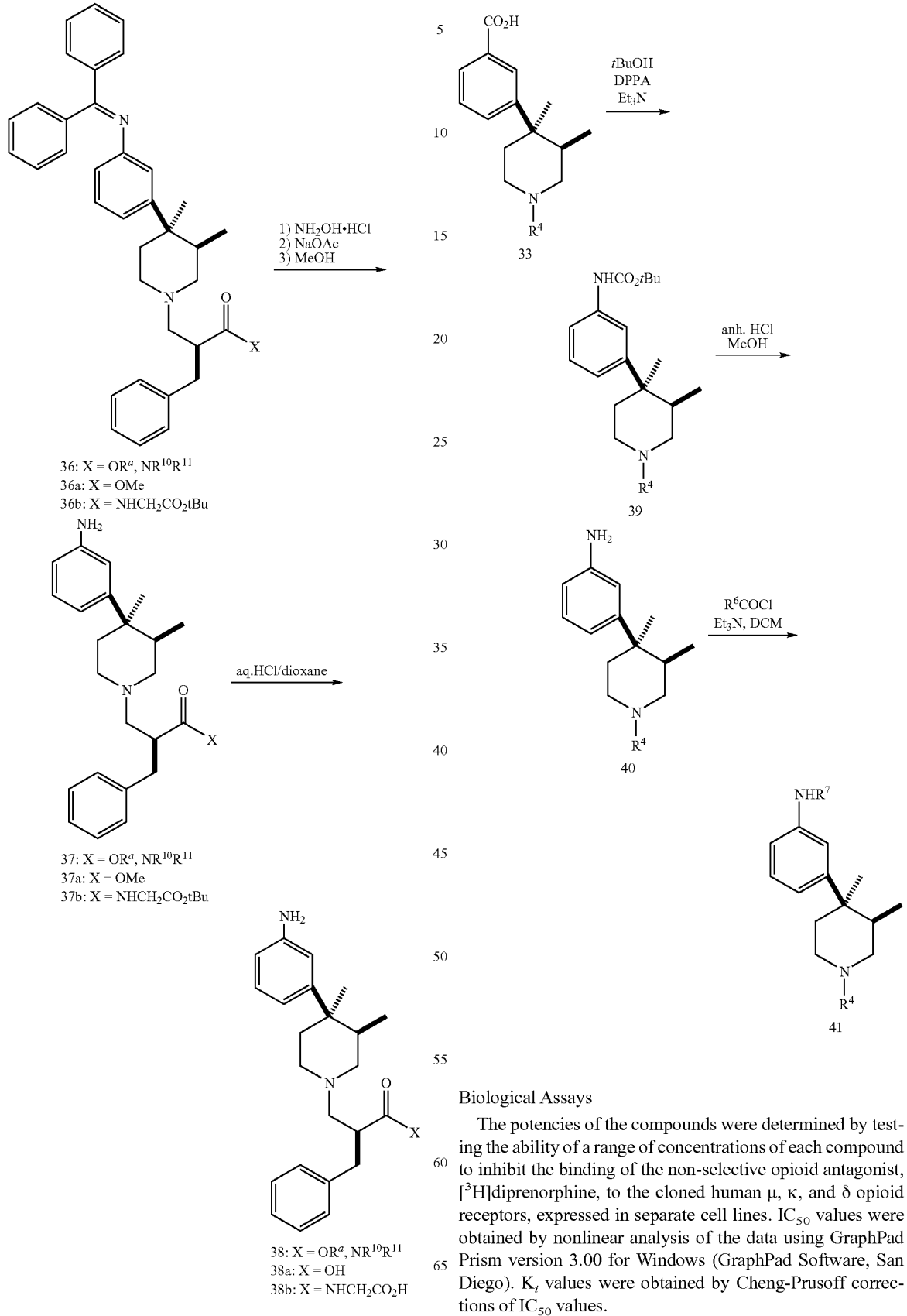

Biological Assays

The potencies of the compounds were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. IC$_{50}$ values were obtained by nonlinear analysis of the data using GraphPad Prism version 3.00 for Windows (GraphPad Software, San Diego). K$_i$ values were obtained by Cheng-Prusoff corrections of IC$_{50}$ values.

Receptor Binding (In Vitro Assay)

The receptor binding method (DeHaven and DeHaven-Hudkins, 1998) was a modification of the method of Raynor et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - \text{Log}EC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and Log EC50 is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand and $K_d$ is the equilibrium dissociation constant for the radioligand.

The potencies of the antagonists were assessed by their abilities to inhibit agonist-stimulated [$^{35}$S]GTPγS binding to membranes containing the cloned human μ, κ, or δ opioid receptors. The agonists used were loperamide for the μ opioid receptor, U50488H for the κ opioid receptor, and BW373U86 for the δ opioid receptor.

To determine the $IC_{50}$ value, which was the concentration to give half-maximal inhibition of agonist-stimulated [$^{35}$S]GTPγS binding, the amount of [$^{35}$S]GTPγS bound in the presence of a fixed concentration of agonist and various concentrations of antagonist was measured. The fixed concentration of agonist was the $EC_{80}$ for the agonist, which was the concentration to give 80% of the relative maximum stimulation of [$^{35}$S]GTPγS binding. The $IC_{50}$ value was determined from a best nonlinear regression fit of the data to the following equation, $$Y = \text{Bottom} + \frac{(\text{Top} - \text{Bottom})}{1 + 10^{X - \text{Log}EC50}}$$

where Y is the amount of [$^{35}$S]GTPγS bound at each concentration of antagonist, Bottom is the calculated amount of [$^{35}$S]GTPγS bound in the presence of an infinite concentration of antagonist, Top is the calculated amount of [$^{35}$S]GTPys bound in the absence of added antagonist, X is the logarithm of the concentration of antagonist, and Log $IC_{50}$ is the logarithm of the concentration of antagonist where the amount of [$^{35}$S]GTPγS bound is halfway between Bottom and Top. The nonlinear regression fit was performed using GraphPad Prism® version 3.00 for Windows (GraphPad Software, San Diego, Calif.).

The compounds described in Tables 1-4 (examples 1-60) were tested for their affinity towards the mu, delta and kappa opioid receptors. All of these compounds bind with affinity less than 100 μM to the μ, δ and κ opioid receptors. These compounds displayed various degree of selectivity mu versus delta, mu versus kappa and kappa versus delta The activity of selected ligands was also evaluated in vitro. Numerous compounds were found to be pure antagonist at the mu opioid receptor (no agonist activity detectable at concentration >10 μM). As examples, compound 28 (Table 1) binds to the μ, δ and κ opioid receptors with affinity (expressed as $K_i$ value) of 19 nM, 1333 nM and 200 0 nM, respectively). Furthermore, the compound 28 displayed potent in vitro antagonist activity ($IC_{50}$=3.4 nM). The compound 58 (Table 2) binds to the μ, δ and κ opioid receptors with affinity (expressed as $K_i$ value) of 2.6 nM, 85 nM and 1080 nM, respectively). Furthermore, the compound 58 displayed potent in vitro antagonist activity ($IC_{50}$=3.0 nM).

Mouse Gastrointestinal Transit (GIT) Assay (In Vivo Assay)

Male Swiss-Webster mice (25-30 g) obtained from Ace Animals (Boyertown, Pa.) were used for all experiments. Mice were housed 4/cage in polycarbonate cages with food and water available ad libitum. Mice were on a 12 hours light:dark schedule with lights on at 6:30 a.m. All experiments were performed during the light cycle. Mice were fasted the night before the experiment, with water available ad libitum.

Mice were administered vehicle (10% DMSO:20% Cremophor EL:70% saline) or test compound (10 mg/kg) orally 2 or 6 hours before determination of GIT. Compounds were administered in a volume of 0.1 ml/10 g of body weight. Morphine (3 mg/kg) or vehicle (0.9% saline) was administered s.c. 35 min prior to determination of GIT. Ten minutes after the morphine treatment, mice were administered 0.2 ml of a charcoal meal orally. The charcoal meal consisted of a slurry of charcoal, flour, and water in the following ratio (1:2:8, w:w:v). Twenty-five minutes after receiving the charcoal meal, the mice were euthanized with $CO_2$ and GIT determined.

GIT is expressed as the % GIT by the following formula:

$$\frac{(\text{distance to leading edge of charcoal meal (cm)})}{(\text{total length of the small intestine (cm)})} \times 100$$

For each compound a % Antagonism (% A) value was determined for the 2 and 6 hr antagonist pretreatment. Using the mean % GIT for each treatment group, % A was calculated using the following formula:

$$1 - \left( \frac{\text{mean vehicle response} - \binom{\text{mean antagonist} + \text{morphine response}}{}}{(\text{mean vehicle response} - \text{mean morphine response})} \right) \times 100$$

The antagonist activity of selected compounds was evaluated using the Mouse Gastrointestinal Transit (GIT) Assay (in vivo assay). Numerous compounds tested were found to have antagonist activity in this assay ranging from 20% to 100%. For example, the compound 28 (10 mg/kg; p.o.) displays 86% antagonism at 2 h and 71% at 6 h. The compound 58 (10 mg/kg; p.o.) displays 92% antagonism at 2 h and 61% at 6 h.

TABLE 1

DERIVATIVES OF FORMULA I ($R^1$ is $CO_2H$)

| Example | Structure | Name | $[M + H]^+$ |
|---|---|---|---|
| 1 | 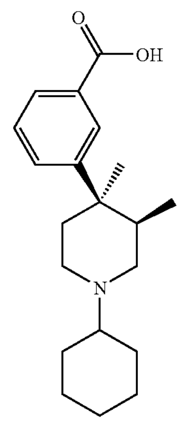 | 3-(1-Cyclohexyl-3R,4R-dimethyl-piperidin-4-yl)-benzoic acid | 316 |
| 2 | 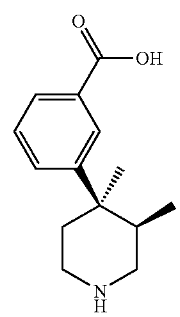 | 3-(3R,4R-Dimethyl-piperidin-4-yl)-benzoic acid | 234 |
| 3 | 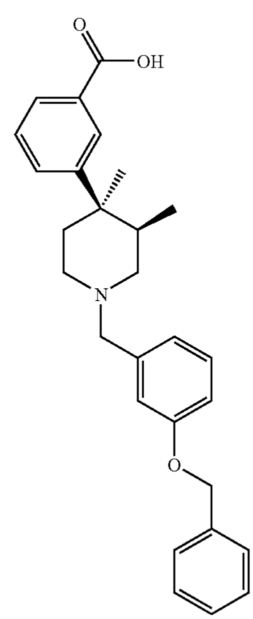 | 3-[1-(3-Benzyloxy-benzyl)-3R,4R-dimethyl-piperidin-4-yl]-benzoic acid | 430 |

TABLE 1-continued

| DERIVATIVES OF FORMULA I ($R^1$ is $CO_2H$) | | | |
|---|---|---|---|
| Example | Structure | Name | $[M + H]^+$ |
| 4 | | 3-(1-Biphenyl-4-ylmethyl-3R,4R-dimethyl-piperidin-4-yl)-benzoic acid | 400 |
| 5 | | [3R,4R-Dimethyl-1-(3-phenoxy-benzyl)-piperidin-4-yl]-benzoic acid | 416 |
| 6 | | 3-[1-(4-Dimethylamino-benzyl)-3R,4R-dimethyl-piperidin-4-yl]-benzoic acid | 367 |

TABLE 1-continued

DERIVATIVES OF FORMULA I ($R^1$ is $CO_2H$)

| Example | Structure | Name | [M + H]⁺ |
|---|---|---|---|
| 7 | 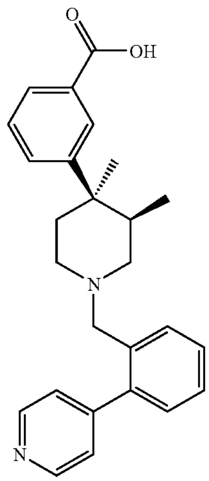 | 3-[3R,4R-Dimethyl-1-(2-pyridin-4-yl-benzyl)-piperidin-4-yl]-benzoic acid | 401 |
| 8 | 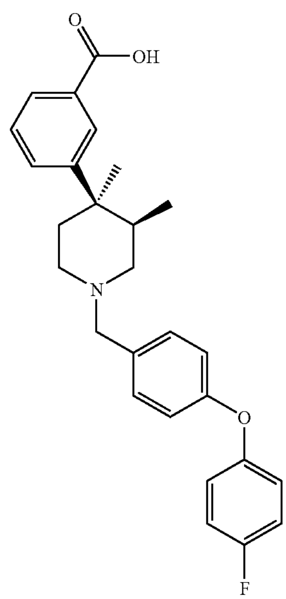 | 3-{1-[4-(4-Fluoro-phenoxy)-benzyl]-3R,4R-dimethyl-piperidin-4-yl}-benzoic acid | 434 |
| 9 | 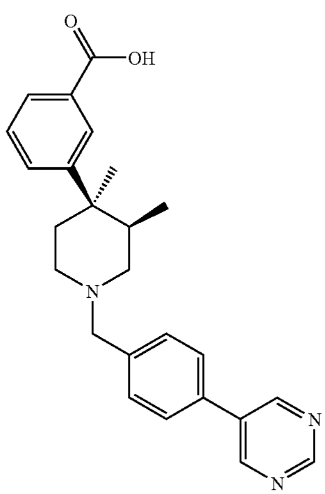 | 3-[3R,4R-Dimethyl-1-(4-pyrimidin-5-yl-benzyl)-piperidin-4-yl]-benzoic acid | 402 |

TABLE 1-continued

| DERIVATIVES OF FORMULA I (R¹ is CO₂H) | | | |
|---|---|---|---|
| Example | Structure | Name | [M + H]⁺ |
| 10 | | 3-[3R,4R-Dimethyl-1-(4-pyridin-3-yl-benzyl)-piperidin-4-yl]-benzoic acid | 401 |
| 11 | | 3-[3R,4R-Dimethyl-1-(4-pyridin-4-yl-benzyl)-piperidin-4-yl]-benzoic acid | 401 |
| 12 | | 3-{1-[4-(3-Dimethylamino-propoxy)-benzyl]-3R,4R-dimethyl-piperidin-4-yl}-benzoic acid | 425 |

TABLE 1-continued
DERIVATIVES OF FORMULA I ($R^1$ is $CO_2H$)
| Example | Structure | Name | [M + H]+ |
|---|---|---|---|
| 13 | 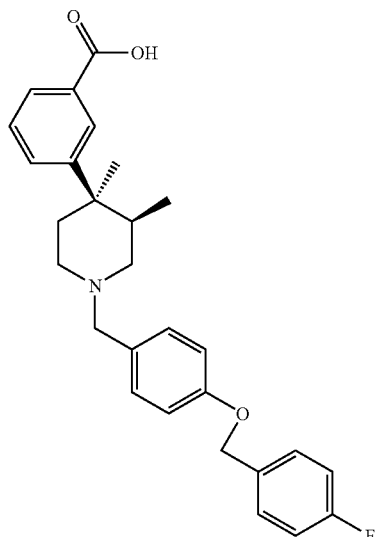 | 3-{1-[4-(4-Fluoro-benzyloxy)-benzyl]-3R,4R-dimethyl-piperidin-4-yl}-benzoic acid | 448 |
| 14 | 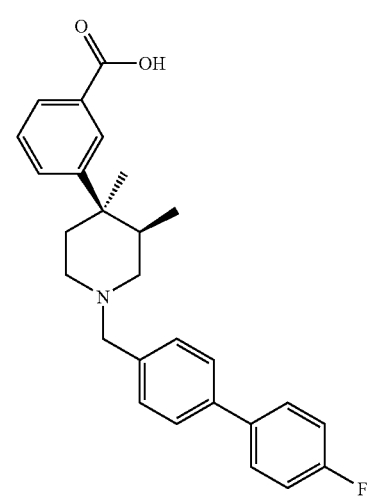 | 3-[1-(4'-Fluoro-biphenyl-4-ylmethyl)-3R,4R-dimethyl-piperidin-4-yl]-benzoic acid | 418 |
| 15 | 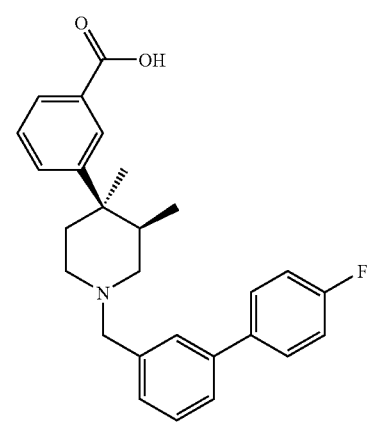 | 3-[1-(4'-Fluoro-biphenyl-3-ylmethyl)-3R,4R-dimethyl-piperidin-4-yl]-benzoic acid | 418 |

TABLE 1-continued
| | DERIVATIVES OF FORMULA I (R¹ is CO₂H) | | |
|---|---|---|---|
| Example | Structure | Name | [M + H]⁺ |
| 16 | 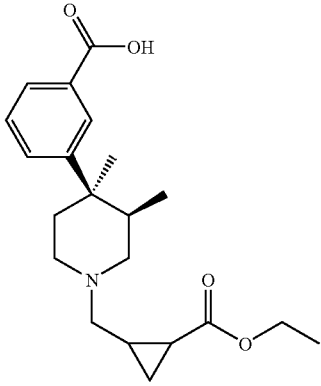 | 3-[1-(2-Ethoxycarbonyl-cyclopropylmethyl)-3R,4R-dimethyl-piperidin-4-yl]-benzoic acid | 360 |
| 17 | 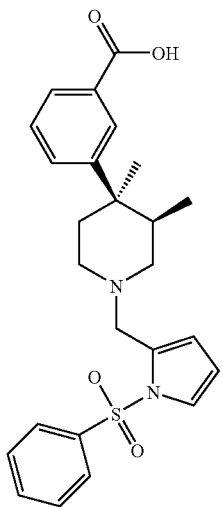 | 3-[1-(1-Benzenesulfonyl-1H-pyrrol-2-ylmethyl)-3R,4R-dimethyl-piperidin-4-yl]-benzoic acid | 453 |
| 18 | 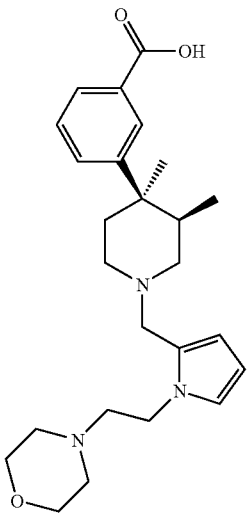 | 3-{3R,4R-Dimethyl-1-[1-(2-morpholin-4-yl-ethyl)-1H-pyrrol-2-ylmethyl]-piperidin-4-yl}-benzoic acid | 424 |

TABLE 1-continued

| | DERIVATIVES OF FORMULA I ($R^1$ is $CO_2H$) | | |
|---|---|---|---|
| Example | Structure | Name | $[M + H]^+$ |
| 19 | | 3-[1-(1-Isoxazol-3-yl-1H-pyrrol-2-ylmethyl)-3R,4R-dimethyl-piperidin-4-yl]-benzoic acid | 380 |
| 20 | | 3-(1-Bicyclo[2.2.1]hept-5-en-2-ylmethyl-3R,4R-dimethyl-piperidin-4-yl)-benzoic acid | 340 |
| 21 | | 3-[3R,4R-Dimethyl-1-(4-methylsulfanyl-benzyl)-piperidin-4-yl]-benzoic acid | 370 |

TABLE 1-continued

DERIVATIVES OF FORMULA I ($R^1$ is $CO_2H$)

| Example | Structure | Name | [M + H]+ |
|---------|-----------|------|----------|
| 22 | 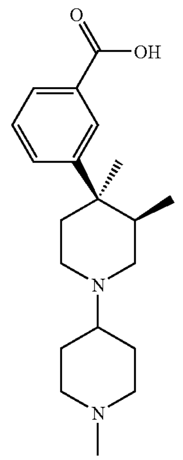 | 3-(3R,4R,1'-Trimethyl-[1,4']bipiperidinyl-4-yl)-benzoic acid | 331 |
| 23 | 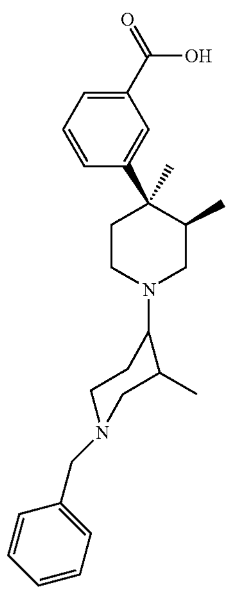 | 3-(1'-Benzyl-3R,4R,3'-trimethyl-[1,4']bipiperidinyl-4-yl)-benzoic acid | 421 |
| 24 | 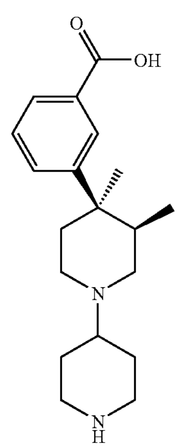 | 3-(3R,4R-Dimethyl-[1,4']bipiperidinyl-4-yl)-benzoic acid | 317 |

TABLE 1-continued
DERIVATIVES OF FORMULA I ($R^1$ is $CO_2H$)
| Example | Structure | Name | $[M + H]^+$ |
|---|---|---|---|
| 25 | 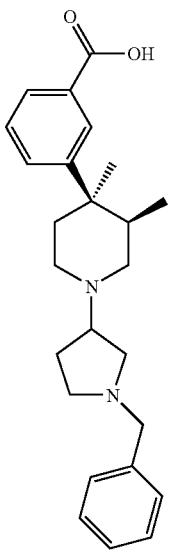 | 3-[1-1-(1-Benzyl-pyrrolidin-3-yl)-3R,4R-dimethyl-piperidin-4-yl]-benzoic acid | 393 |
| 26 | 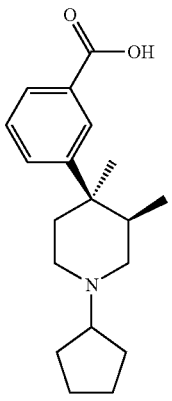 | 3-(1-Cyclopentyl-3R,4R-dimethyl-piperidin-4-yl)-benzoic acid | 302 |
| 27 | 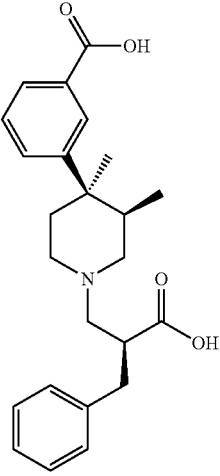 | 3-[1-(2S-Carboxy-3-phenyl-propyl)-3R,4R-dimethyl-piperidin-4-yl]-benzoic acid | 396 |

TABLE 1-continued

DERIVATIVES OF FORMULA I ($R^1$ is $CO_2H$)

| Example | Structure | Name | [M + H]⁺ |
|---|---|---|---|
| 28 | 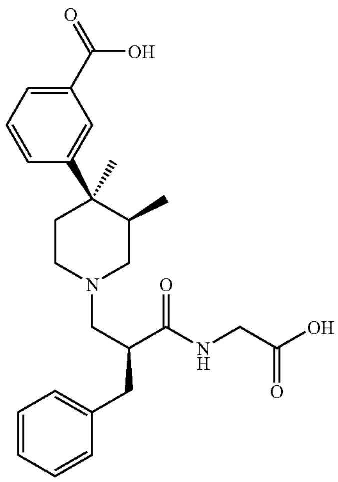 | [[2(R)-[[4(R)-(3-carboxyphenyl)-3(R),4-dimethyl-1-piperidinyl]methyl]-1-oxo-3-phenylpropyl]amino]acetic Acid | 453 |
| 29 | 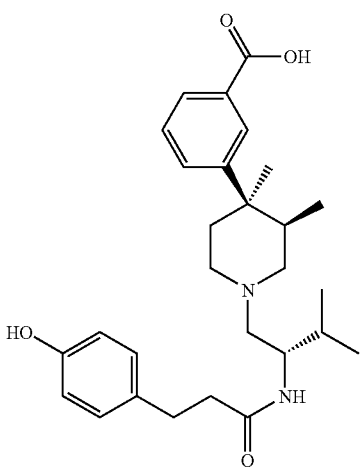 | 3-(1-{2-[3-(4-Hydroxyphenyl)-propionylamino]-3-methyl-butyl}-3R,4R-dimethyl-piperidin-4-yl)benzoic acid | 467 |

TABLE 2

DERIVATIVES OF FORMULA I ($R^1$ is $CONH_2$)

| Example | Structure | Name | [M + H]⁺ |
|---|---|---|---|
| 30 | 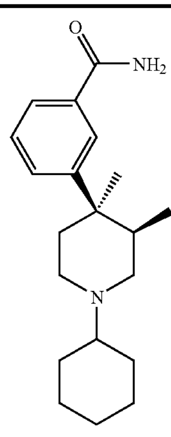 | 3-(1-Cyclohexyl-3R,4R-dimethyl-piperidin-4-yl)-benzamide | 315 |

TABLE 2-continued

DERIVATIVES OF FORMULA I ($R^1$ is $CONH_2$)

| Example | Structure | Name | $[M + H]^+$ |
|---|---|---|---|
| 31 | 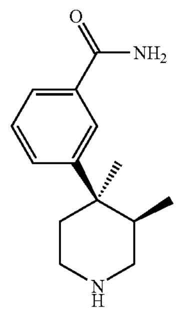 | 3-(3R,4R-Dimethyl-piperidin-4-yl)-benzamide | 233 |
| 32 | 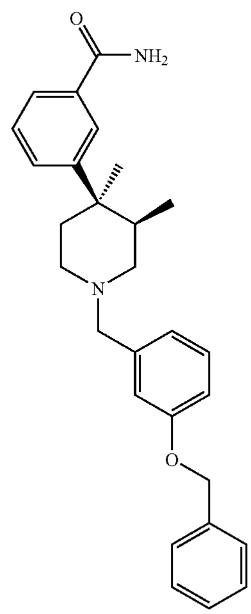 | 3-[1-(3-Benzyloxy-benzyl)-3R,4R-dimethyl-piperidin-4-yl]-benzamide | 429 |
| 33 | 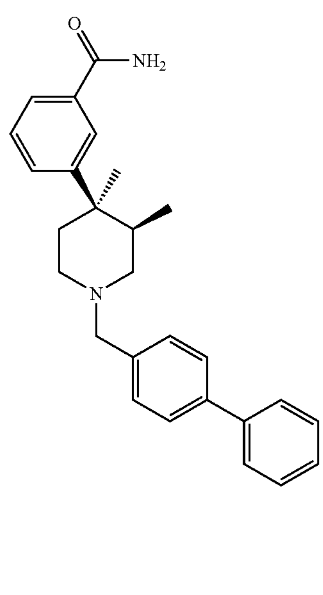 | 3-(1-Biphenyl-4-ylmethyl-3R,4R-dimethyl-piperidin-4-yl)-benzamide | 399 |

TABLE 2-continued

DERIVATIVES OF FORMULA I ($R^1$ is $CONH_2$)

| Example | Structure | Name | [M + H]+ |
|---|---|---|---|
| 34 | 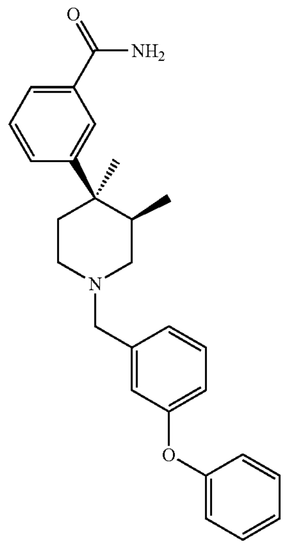 | 3-[3R,4R-Dimethyl-1-(3-phenoxy-benzyl)-piperidin-4-yl]-benzamide | 415 |
| 35 | 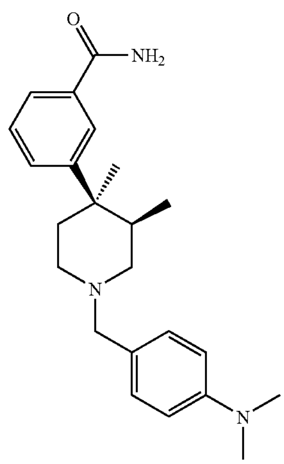 | 3-[1-(4-Dimethylamino-benzyl)-3R,4R-dimethyl-piperidin-4-yl]-benzamide | 366 |
| 36 | 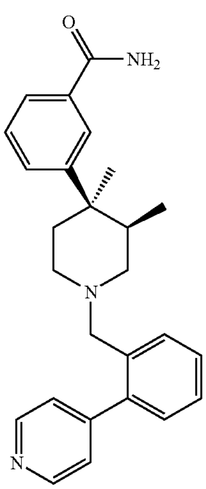 | [3R,4R-Dimethyl-1-(2-pyridin-4-yl-benzyl)-piperidin-4-yl]-benzamide | 400 |

TABLE 2-continued

DERIVATIVES OF FORMULA I (R¹ is CONH₂)

| Example | Structure | Name | [M + H]⁺ |
|---------|-----------|------|----------|
| 37 | 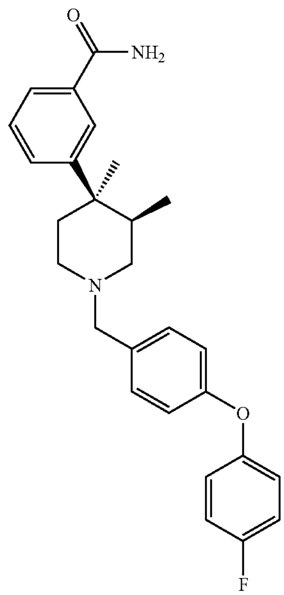 | 3-{1-[4-(4-Fluoro-phenoxy)-benzyl]-3R,4R-dimethyl-pipendin-4-yl}-benzamide | 433 |
| 38 | 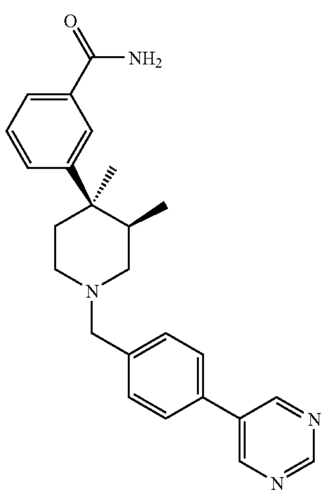 | 3-[3R,4R-Dimethyl-1-(4-pyrimidin-5-yl-benzyl)-piperidin-4-yl]-benzamide | 401 |
| 39 | 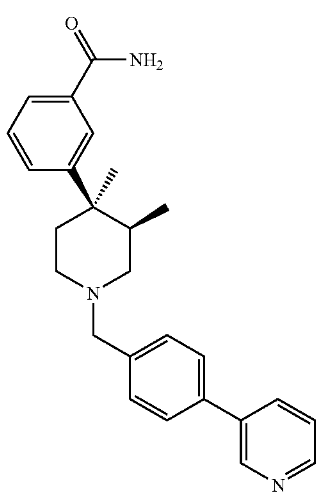 | 3-[3R,4R-Dimethyl-1-(4-pyridin-3-yl-benzyl)-piperidin-4-yl]-benzamide | 400 |

TABLE 2-continued

DERIVATIVES OF FORMULA I ($R^1$ is $CONH_2$)

| Example | Structure | Name | [M + H]$^+$ |
|---|---|---|---|
| 40 | 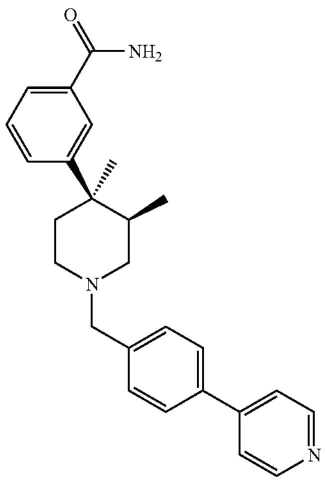 | 3-[3R,4R-Dimethyl-1-(4-pyridin-4-yl-benzyl)-piperidin-4-yl]-benzamide | 400 |
| 41 | 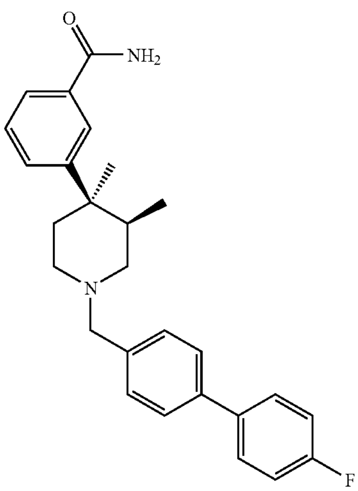 | 3-[1-(4'-Fluoro-biphenyl-4-ylmethyl)-3R,4R-dimethyl-piperidin-4-yl]-benzamide | 417 |
| 42 | 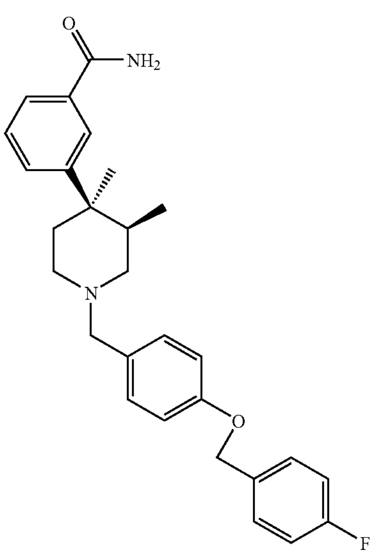 | 3-{1-[4-(4-Fluoro-benzyloxy)-benzyl]-3R,4R-dimethyl-piperidin-4-yl}-benzamide | 447 |

TABLE 2-continued
DERIVATIVES OF FORMULA I (R¹ is CONH₂)
| Example | Structure | Name | [M + H]⁺ |
|---|---|---|---|
| 43 | 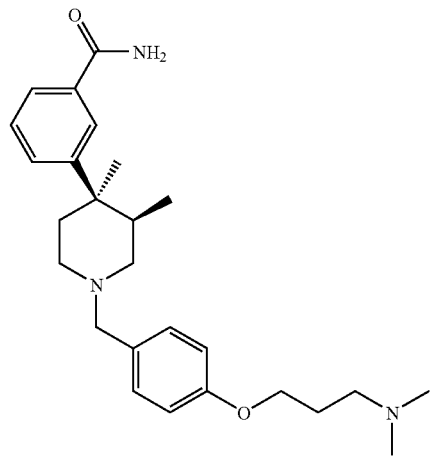 | 3-{1-[4-(3-Dimethylamino-propoxy)-benzyl]-3R,4R-dimethyl-piperidin-4-yl}-benzamide | 424 |
| 44 | 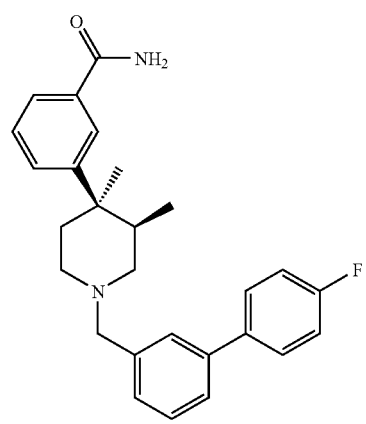 | 3-[1-(4'-Fluoro-biphenyl-3-ylmethyl)-3R,4R-dimethyl-piperidin-4-yl]-benzamide | 417 |
| 45 | 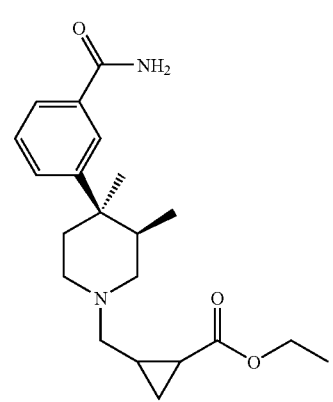 | 3-[1-(2-Ethoxycarbonyl-cyclopropylmethyl)-3R,4R-dimethyl-piperidin-4-yl]-benzamide | 359 |

TABLE 2-continued

| DERIVATIVES OF FORMULA I ($R^1$ is $CONH_2$) | | | |
|---|---|---|---|
| Example | Structure | Name | $[M + H]^+$ |
| 46 | | 3-[1-(1-Benzenesulfonyl-1H-pyrrol-2-ylmethyl)-3R,4R-dimethyl-piperidin-4-yl]-benzamide | 452 |
| 47 | | 3-{3R,4R-Dimethyl-1-[1-(2-morpholin-4-yl-ethyl)-1H-pyrrol-2-ylmethyl]-piperidin-4-yl}-benzamide | 425 |
| 48 | | 3-[1-(1-Isoxazol-3-yl-1H-pyrrol-2-ylmethyl)-3R,4R-dimethyl-piperidin-4-yl]-benzamide | 379 |

TABLE 2-continued

DERIVATIVES OF FORMULA I ($R^1$ is $CONH_2$)

| Example | Structure | Name | [M + H]+ |
|---|---|---|---|
| 49 | 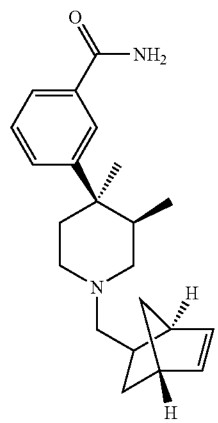 | 3-(1-Bicyclo[2.2.1]hept-5-en-2-ylmethyl-3R,4R-dimethyl-piperidin-4-yl)-benzamide | 339 |
| 50 | 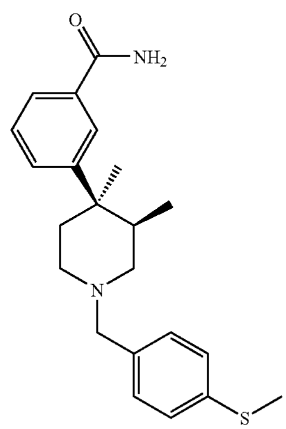 | 3-[3R,4R-Dimethyl-1-(4-methylsulfanyl-benzyl)-piperidin-4-yl]-benzamide | 339 |
| 51 | 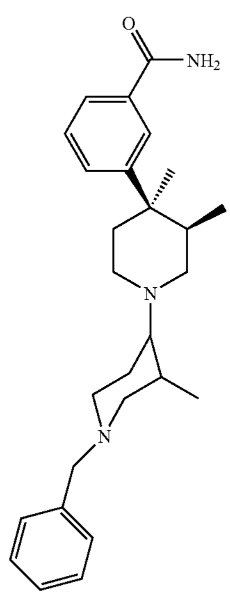 | 3-(1'-Benzyl-3R,4R,3'-trimethyl-[1,4']bipiperidinyl-4-yl)-benzamide | 420 |

TABLE 2-continued

DERIVATIVES OF FORMULA I ($R^1$ is $CONH_2$)

| Example | Structure | Name | [M + H]⁺ |
|---|---|---|---|
| 52 | 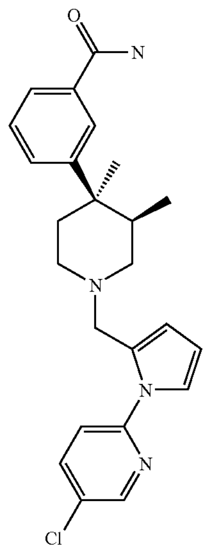 | 3-{1-[1-(5-Chloro-pyridin-2-yl)-1H-pyrrol-2-ylmethyl]-3R,4R-dimethyl-piperidin-4-yl}-benzamide | 423 |
| 53 | 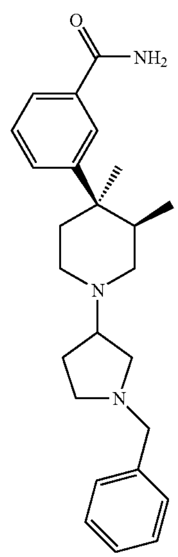 | 3-[1-(1-Benzyl-pyrrolidin-3-yl)-3R,4R-dimethyl-piperidin-4-yl]-benzamide | 392 |
| 54 | 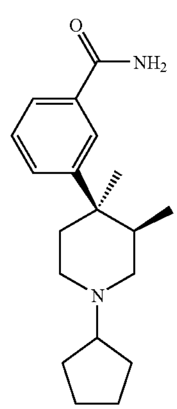 | 3-(1-Cyclopentyl-3R,4R-dimethyl-piperidin-4-yl)-benzamide | 301 |

TABLE 2-continued

DERIVATIVES OF FORMULA I (R¹ is CONH₂)

| Example | Structure | Name | [M + H]⁺ |
|---|---|---|---|
| 55 | 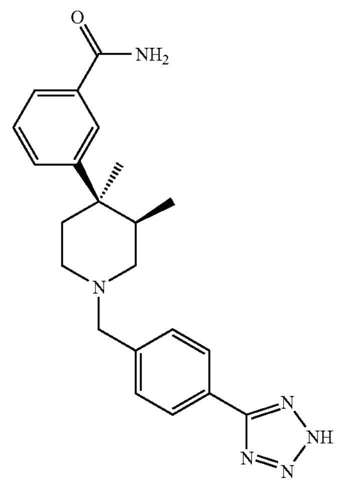 | 3-{3R,4R-Dimethyl-1-[4-(2H-tetrazol-5-yl)-benzyl]-piperidin-4-yl}-benzamide | 391 |
| 56 | 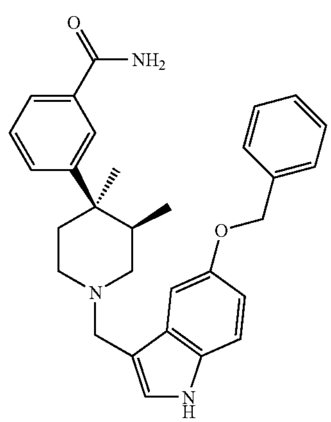 | 3-[1-(5-Benzyloxy-1H-indol-3-ylmethyl)-3R,4R-dimethyl-piperidin-4-yl]-benzamide | 468 |
| 57 | 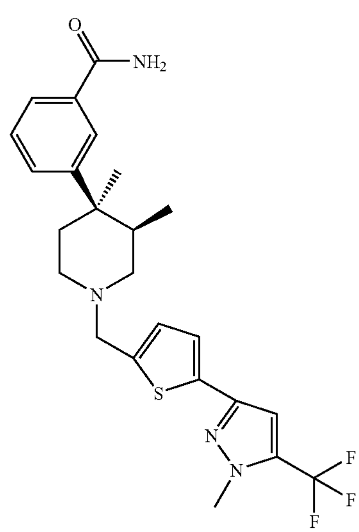 | 3-{3R,4R-Dimethyl-1-[5-(1-methyl-5-trifluoromethyl-1H-pyrazol-3-yl)-thiophen-2-ylmethyl]-piperidin-4-yl}-benzamide | 477 |

TABLE 2-continued

DERIVATIVES OF FORMULA I (R¹ is CONH₂)

| Example | Structure | Name | [M + H]⁺ |
|---|---|---|---|
| 58 | 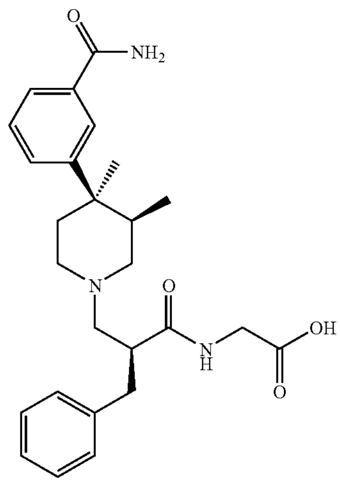 | [[2(R)-[[4(R)-(3-amidophenyl)-3(R),4-dimethyl-1-piperidinyl]methyl]-1-oxo-3-phenylpropyl]amino]acetic Acid | 424 |
| 59 | 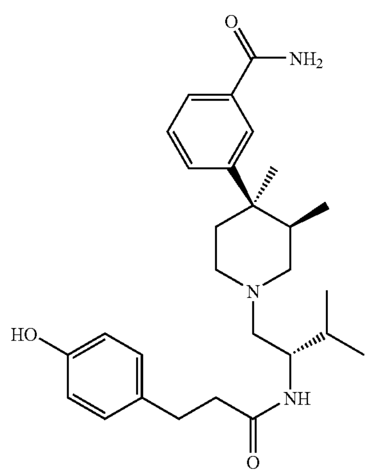 | 3-(1-{2-[3-(4-Hydroxyphenyl)-propionylamino]-3-methyl-butyl}-3R,4R-dimethyl-piperidin-4-yl)benzamide | 466 |

TABLE 3

DERIVATIVES OF FORMULA I (R¹ is NH₂)

| Example | Structure | Name | [M + H]⁺ |
|---|---|---|---|
| 60 | 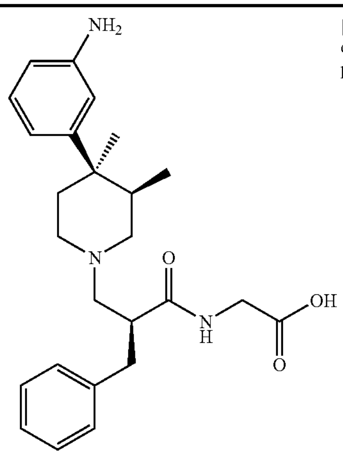 | [[2(R)-[[4(R)-(3-aminophenyl)-3(R),4-dimethyl-1-piperidinyl]methyl]-1-oxo-3-phenylpropyl]amino]acetic Acid | 424 |

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound according of formula I:

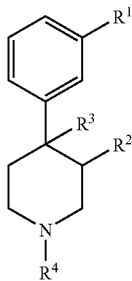

I wherein:
$R^1$ is —C(=O)OR$^5$, —C(=O)NR$^6$R$^7$, or —NR$^6$R$^7$;
$R^2$ and $R^3$ are each independently alkyl or alkenyl;
$R^4$ is:
  H,
  cycloalkyl,
  heterocycloalkyl, or
  $C_{1-10}$ alkyl which is substituted with at least one:
    substituted aryl, wherein at least one of said aryl substituents is other than OH, nitro, amino, halo, CN, CH$_2$CN, CONH$_2$, $C_{1-4}$ alkyl, $C_{1-4}$ alkoxy, or $C_{1-5}$ alkanoyl (which latter three groups are optionally substituted by one or more halo atoms),
    aryloxyaryl,
    -aryl-N(H)R$^b$,
    -aryl-N(R$^b$)R$^b$,
    heteroarylaryl,
    alkoxyaryl, wherein the carbon chain of said alkoxy is interrupted by a nitrogen atom,
    substituted alkoxyaryl, provided that when one or more substituents are present on the alkoxy group, at least one of said substituents is other than halo,
    substituted cycloalkyl,
    RS(=O)$_p$ substituted heteroaryl,
    RS(=O)$_p$ substituted heterocycloalkyl,
    RS(=O)$_p$ substituted aryl,
    heterocycloalkylheteroaryl,
    heteroarylheteroaryl,
    bicycloalkyl,
    bicycloalkenyl,
    carboxy,
    —CO$_2$R$^a$,
    —C(=O)N(R$^{6a}$)—R$^{6b}$—CO$_2$H,
    —C(=O)N(R$^{6a}$)—R$^{6b}$—CO$_2$R,
    —C(=O)N(R$^{6a}$)—R$^{6b}$—C(=O)NR$^{7a}$R$^{7b}$,
    —N(R$^{7c}$)C(=O)R$^{7d}$,
    —N(R$^{7c}$)S(=O)$_2$R$^{7d}$,
    aralkoxyaryl,
    substituted arylheteroaryl, or
    substituted alkoxyheteroaryl, provided that when one or more substituents are present on the alkoxy group, at least one of said substituents is other than halo;

p is 0, 1, or 2;

R is alkyl, aralkyl, or aryl;

$R^a$ is H, alkyl, alkenyl, cycloalkyl, aryl, or heteroaryl, provided that $R^a$ is not $C_{1-6}$ alkyl;

each $R^b$ is independently alkyl, cycloalkyl, aralkyl, or aryl, $R^{6a}$ is H, alkyl, aralkyl, cycloalkyl, alkenyl, aryl, heteroaralkyl, or heteroaryl;

$R^{6b}$ is lower alkylene, or lower aralkylene or, together with the nitrogen atom to which they are attached, $R^{6a}$ and $R^{6b}$ form a 4- to 7-membered heterocycloalkyl ring;

$R^{7a}$ and $R^{7b}$ are each independently H, alkyl, cycloalkyl, heterocycloalkyl, heteroaryl, aralkyl, or aryl, or together with the nitrogen atom to which they are attached, $R^{7a}$ and $R^{7b}$ form a 4- to 7-membered heterocycloalkyl ring, provided that at least one of $R^{7a}$ and $R^{7b}$ is other than H;

$R^{7c}$ and $R^{7d}$ are each independently H, alkyl, cycloalkyl, heterocycloalkyl, heteroaryl, aralkyl, or aryl;

$R^5$ is H or alkyl; and each $R^6$ and $R^7$ is independently H, alkyl, or —C(=O)R, or, together with the nitrogen atom to which they are attached, $R^6$ and $R^7$ form a 4- to 7-membered heterocycloalkyl ring, provided that no more than one of $R^6$ and $R^7$ is —C(=O)R, and provided that when $R^1$ is NR$^6$R$^7$, $R^4$ can also be aralkyl;

provided that when $R^4$ is H and $R^2$ and $R^3$ are each independently alkyl, then $R^1$ is —C(=O)NR$^6$R$^7$ or —NR$^6$R$^7$, wherein at least one of $R^6$ and $R^7$ is —C(=O)R, or, $R^6$ and $R^7$ taken together with the nitrogen atom to which they are attached, form a 4- to 7-membered heterocycloalkyl ring;

or a stereoisomer, pharmaceutically acceptable salt, or N-oxide thereof, provided that $R^2$ and $R^3$ are not in the cis stereoisomer conformation when both $R^2$ and $R^3$ are methyl.

2. A compound according to claim 1, wherein said compound is a compound of formula Ia:

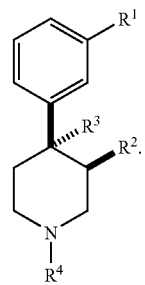

Ia

3. A compound according to claim 2, wherein $R^2$ is methyl.

4. A compound according to claim 3, wherein $R^3$ is methyl.

5. A compound according to claim 4, wherein said compound is a compound of formula IIa:

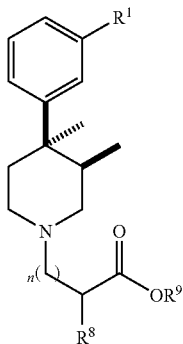

wherein:
R⁸ is alkyl, aralkyl, cycloalkyl, alkylcycloalkyl, aryl, heteroaryl, or heteroaralkyl;
R⁹ is H, alkyl, alkenyl, cycloalkyl, aryl, or heteroaryl provided that R⁹ is not $C_{1-6}$ alkyl; and
n is an integer from 1 to 3.

6. A compound according to claim 5, wherein said compound is a compound of formula IIIa:

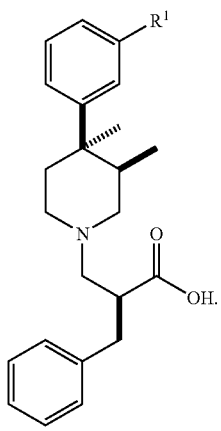

7. A compound selected from the group consisting of:
3-(3R,4R-dimethyl-piperidin-4-yl)-benzoic acid;
3-(3R,4R-dimethyl-[1,4']bipiperidinyl-4-yl)-benzoic acid; and
3-(3R,4R-dimethyl-piperidin-4-yl)-benzamide;
or a pharmaceutically acceptable salt thereof.

8. A pharmaceutical composition, comprising:
a pharmaceutically acceptable carrier; and
a therapeutically effective amount of a compound according to claim 1.

9. A pharmaceutical composition according to claim 8, further comprising a therapeutically effective amount of at least one opioid.

10. A pharmaceutical composition according to claim 9, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

11. A method for treating gastrointestinal dysfunction, comprising the step of:
administering to a patient in need thereof, an effective amount of a compound according to claim 1.

12. A method for treating ileus, comprising the step of:
administering to a patient in need thereof, an effective amount of a compound according to claim 1.

13. A method for treating a side effect associated with an opioid, comprising the step of:
administering to a patient in need thereof, an effective amount of a compound according to claim 1.

14. A method according to claim 13, further comprising administering to the patient an effective amount of at least one opioid.

15. A method according to claim 13, wherein said side effect is selected from constipation, nausea or vomiting.

16. A method according to claim 13, wherein said administering step occurs before, during or after a step of administering at least one opioid.

17. A method of treating pain, comprising the step of:
administering to a patient in need thereof, an effective amount of an opioid; and
an effective amount of a compound according to claim 1.

18. A method according to claim 14, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

19. A method according to claim 17, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

20. A pharmaceutical composition, comprising:
a pharmaceutically acceptable carrier; and
a therapeutically effective amount of a compound according to claim 7.

21. A pharmaceutical composition according to claim 20, further comprising a therapeutically effective amount of at least one opioid.

22. A pharmaceutical composition according to claim 21, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

23. A method for treating gastrointestinal dysfunction, comprising the step of:
administering to a patient in need thereof, an effective amount of a compound according to claim 7.

24. A method for treating ileus, comprising the step of:
administering to a patient in need thereof, an effective amount of a compound according to claim 7.

25. A method for treating a side effect associated with an opioid, comprising the step of:
administering to a patient in need thereof, an effective amount of a compound according to claim 7.

26. A method according to claim 25, further comprising administering to the patient an effective amount of at least one opioid.

27. A method according to claim 25, wherein said side effect is selected from constipation, nausea or vomiting.

28. A method according to claim 25, wherein said administering step occurs before, during or after a step of administering at least one opioid.

29. A method of treating pain, comprising the step of:
administering to a patient in need thereof, an effective amount of an opioid; and
an effective amount of a compound according to claim 7.

30. A method according to claim 29, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

31. A method of binding opioid receptors in a patient in need thereof, comprising the step of:
administering to said patient a therapeutically effective amount of a compound according of formula Ib:

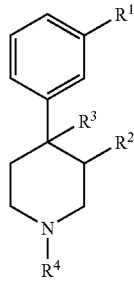

Ib wherein:
$R^1$ is —C(=O)OR$^5$, —C(=O)NR$^6$R$^7$, —NR$^6$R$^7$, or —CH$_2$OR$^5$;
$R^2$ and $R^3$ are each independently alkyl or alkenyl;
$R^4$ is:
H,
cycloalkyl,
heterocycloalkyl, or
$C_{1-10}$ alkyl which is substituted with at least one:
substituted aryl, wherein at least one of said aryl substituents is other than OH, nitro, amino, halo, CN, CH$_2$CN, CONH$_2$, $C_{1-4}$ alkyl, $C_{1-4}$ alkoxy, or $C_{1-5}$ alkanoyl (which latter three groups are optionally substituted by one or more halo atoms),
aryloxyaryl,
-aryl-N(H)R$^b$,
-aryl-N(R$^b$)R$^b$,
heteroarylaryl,
alkoxyaryl, wherein the carbon chain of said alkoxy is interrupted by a nitrogen atom,
substituted alkoxyaryl, provided that when one or more substituents are present on the alkoxy group, at least one of said substituents is other than halo,
substituted cycloalkyl,
RS(=O)$_p$ substituted heteroaryl,
RS(=O)$_p$ substituted heterocycloalkyl,
RS(=O)$_p$ substituted aryl,
heterocycloalkylheteroaryl,
heteroarylheteroaryl,
bicycloalkyl,
bicycloalkenyl,
carboxy,
—CO$_2$R$^a$,
—C(=O)N(R$^{6a}$)—R$^{6b}$—CO$_2$H,
—C(=O)N(R$^{6a}$)—R$^{6b}$CO$_2$R,
—C(=O)N(R$^{6a}$)—R$^{6b}$—C(=)NR$^{7a}$R$^{7b}$,
—N(R$^{7c}$)C(=O)R$^{7d}$,
—N(R$^{7c}$)S(=O)$_2$R$^{7d}$,
aralkoxyaryl,
substituted arylheteroaryl, or
substituted alkoxyheteroaryl, provided that when one or more substituents are present on the alkoxy group, at least one of said substituents is other than halo;
p is 0, 1, or 2;
R is alkyl, aralkyl, or aryl;
$R^a$ is H, alkyl, alkenyl, cycloalkyl, aryl, or heteroaryl, provided that $R^a$ is not $C_{1-6}$ alkyl;
each $R^b$ is independently alkyl, cycloalkyl, aralkyl, or aryl,
$R^{6a}$ is H, alkyl, aralkyl, cycloalkyl, alkenyl, aryl, heteroaralkyl, or heteroaryl;
$R^{6b}$ is lower alkylene, or lower aralkylene or, together with the nitrogen atom to which they are attached, $R^{6a}$ and $R^{6b}$ form a 4- to 7-membered heterocycloalkyl ring;
$R^{7a}$ and $R^{7b}$ are each independently H, alkyl, cycloalkyl, heterocycloalkyl, heteroaryl, aralkyl, or aryl, or together with the nitrogen atom to which they are attached, $R^{7a}$ and $R^{7b}$ form a 4- to 7-membered heterocycloalkyl ring, provided that at least one of $R^{7a}$ and $R^{7b}$ is other than H;
$R^{7c}$ and $R^{7d}$ are each independently H, alkyl, cycloalkyl, heterocycloalkyl, heteroaryl, aralkyl, or aryl;
$R^5$ is H or alkyl; and
each $R^6$ and $R^7$ is independently H, alkyl, or —C(=O)R, or, together with the nitrogen atom to which they are attached, $R^6$ and $R^7$ form a 4- to 7-membered heterocycloalkyl ring, provided that no more than one of $R^6$ and $R^7$ is —C(=O)R, and provided that when $R^1$ is NR$^6$R$^7$, $R^4$ can also be aralkyl;
or a stereoisomer, pharmaceutically acceptable salt, or N-oxide thereof, provided that $R^2$ and $R^3$ are not in the cis stereoisomer conformation when both $R^2$ and $R^3$ are methyl.

32. A method according to claim 31, wherein said compound binds μ opioid receptors.

33. A method according to claim 32, wherein said μ opioid receptors are located in the central nervous system.

34. A method according to claim 32, wherein said μ opioid receptor are located peripherally to the central nervous system.

35. A method according to claim 31, wherein said compound binds κ opioid receptors.

36. A method according to claim 35, wherein said κ opioid receptors are located in the central nervous system.

37. A method according to claim 35, wherein said κ opioid receptors are located peripherally to the central nervous system.

38. A method according to claim 31, wherein said binding antagonizes the activity of said opioid receptors.

39. A method according to claim 31, wherein said compound exhibits activity toward said opioid receptors.

40. A method according to claim 31, wherein said compound does not substantially cross the blood-brain barrier.

41. A method according to claim 31, wherein said patient is in need of treatment of a condition or disease caused by an opioid.

42. A method according to claim 41, wherein said opioid is endogenous.

43. A method according to claim 41, wherein said opioid is exogenous.

44. A pharmaceutical composition, comprising:
a pharmaceutically acceptable carrier; and
a therapeutically effective amount of a compound of formula Ic:

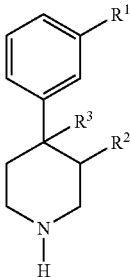

wherein:
R$^1$ is —C(=O)OR$^5$, —C(=O)NR$^6$R$^7$, —NR$^6$R$^7$, or —CH$_2$OR$^5$;
R$^2$ and R$^3$ are each independently alkyl or alkenyl;
R$^5$ is H or alkyl;
each R$^6$ and R$^7$ is independently H, alkyl, or —C(=O)R, or, together with the nitrogen atom to which they are attached, R$^6$ and R$^7$ form a 4- to 7-membered heterocycloalkyl ring, provided that no more than one of R$^6$ and R$^7$ is —C(=O)R; and
R is alkyl, aralkyl, or aryl;
or a stereoisomer, pharmaceutically acceptable salt, or N-oxide thereof, provided that R$^2$ and R$^3$ are not in the cis stereoisomer conformation when both R$^2$ and R$^3$ are methyl.

45. A pharmaceutical composition according to claim 44, further comprising a therapeutically effective amount of at least one opioid.

46. A pharmaceutical composition according to claim 45, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

47. A method for treating gastrointestinal dysfunction, comprising the step of:
administering to a patient in need thereof an effective amount of a compound of formula Ic:

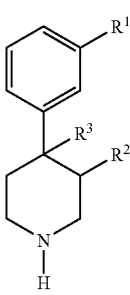

wherein:
R$^1$ is —C(=O)OR$^5$, —C(=O)NR$^6$R$^7$, —NR$^6$R$^7$, or —CH$_2$OR$^5$;
R$^2$ and R$^3$ are each independently alkyl or alkenyl;
R$^5$ is H or alkyl;
each R$^6$ and R$^7$ is independently H, alkyl, or —C(=O)R, or, together with the nitrogen atom to which they are attached, R$^6$ and R$^7$ form a 4- to 7-membered heterocycloalkyl ring, provided that no more than one of R$^6$ and R$^7$ is —C(=O)R; and
R is alkyl, aralkyl, or aryl;
or a stereoisomer, pharmaceutically acceptable salt, or N-oxide thereof, provided that R$^2$ and R$^3$ are not in the cis stereoisomer conformation when both R$^2$ and R$^3$ are methyl.

48. A method for treating ileus, comprising the step of:
administering to a patient in need thereof an effective amount of a compound of formula Ic:

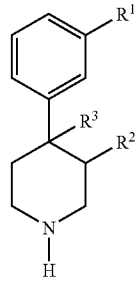

wherein:
R$^1$ is —C(=O)OR$^5$, —C(=O)NR$^6$R$^7$, —NR$^6$R$^7$, or —CH$_2$OR$^5$;
R$^2$ and R$^3$ are each independently alkyl or alkenyl;
R$^5$ is H or alkyl;
each R$^6$ and R$^7$ is independently H, alkyl, or —C(=O)R, or, together with the nitrogen atom to which they are attached, R$^6$ and R$^7$ form a 4- to 7-membered heterocycloalkyl ring, provided that no more than one of R$^6$ and R$^7$ is —C(=O)R; and
R is alkyl, aralkyl, or aryl;
or a stereoisomer, pharmaceutically acceptable salt, or N-oxide thereof, provided that R$^2$ and R$^3$ are not in the cis stereoisomer conformation when both R$^2$ and R$^3$ are methyl.

49. A method for treating a side effect associated with an opioid, comprising the step of:
administering to a patient in need thereof an effective amount of a compound of formula Ic:

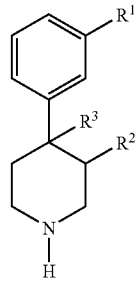

wherein:
R$^1$ is —C(=O)OR$^5$, —C(=O)NR$^6$R$^7$, —NR$^6$R$^7$, or —CH$_2$OR$^5$;
R$^2$ and R$^3$ are each independently alkyl or alkenyl;
R$^5$ is H or alkyl;
each R$^6$ and R$^7$ is independently H, alkyl, or —C(=O)R, or, together with the nitrogen atom to which they are attached, R$^6$ and R$^7$ form a 4- to 7-membered heterocycloalkyl ring, provided that no more than one of R$^6$ and R$^7$ is —C(=O)R; and
R is alkyl, aralkyl, or aryl;

or a stereoisomer, pharmaceutically acceptable salt, or N-oxide thereof, provided that $R^2$ and $R^3$ are not in the cis stereoisomer conformation when both $R^2$ and $R^3$ are methyl.

50. A method according to claim 49, further comprising administering to the patient an effective amount of at least one opioid.

51. A method according to claim 49, wherein said side effect is selected from constipation, nausea or vomiting.

52. A method according to claim 49, wherein said administering step occurs before, during or after a step of administering at least one opioid.

53. A method of treating pain, comprising the step of:
administering to a patient in need thereof an effective amount of an opioid; and
an effective amount of a compound of formula Ic:

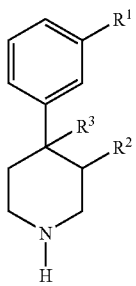

Ic wherein:
$R^1$ is $-C(=O)OR^5$, $-C(=O)NR^6R^7$, $-NR^6R^7$, or $-CH_2OR^5$;
$R^2$ and $R^3$ are each independently alkyl or alkenyl;
$R^5$ is H or alkyl;
each $R^6$ and $R^7$ is independently H, alkyl, or $-C(=O)R$, or, together with the nitrogen atom to which they are attached, $R^6$ and $R^7$ form a 4- to 7-membered heterocycloalkyl ring, provided that no more than one of $R^6$ and $R^7$ is $-C(=O)R$; and
R is alkyl, aralkyl, or aryl;
or a stereoisomer, pharmaceutically acceptable salt, or N-oxide thereof, provided that $R^2$ and $R^3$ are not in the cis stereoisomer conformation when both $R^2$ and $R^3$ are methyl.

54. A method according to claim 50, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

55. A method according to claim 53, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol or mixtures thereof.

* * * * *